(12) United States Patent
MacKay et al.

(10) Patent No.: US 9,102,763 B2
(45) Date of Patent: Aug. 11, 2015

(54) CONTROLLED RELEASE OF OCULAR BIOPHARMACEUTICALS USING BIORESPONSIVE PROTEIN POLYMERS

(75) Inventors: John Andrew MacKay, Pasadena, CA (US); Wan Wang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/559,053

(22) Filed: Jul. 26, 2012

(65) Prior Publication Data

US 2013/0196926 A1    Aug. 1, 2013

Related U.S. Application Data

(60) Provisional application No. 61/511,928, filed on Jul. 26, 2011.

(51) Int. Cl.
| | | |
|---|---|---|
| A61K 47/48 | (2006.01) | |
| C07K 14/78 | (2006.01) | |
| A61K 38/18 | (2006.01) | |
| C07K 14/47 | (2006.01) | |
| A61K 9/00 | (2006.01) | |
| C07K 14/475 | (2006.01) | |

(52) U.S. Cl.
CPC ............ *C07K 14/78* (2013.01); *A61K 9/0048* (2013.01); *A61K 38/18* (2013.01); *A61K 47/48292* (2013.01); *A61K 47/48338* (2013.01); *C07K 14/47* (2013.01); *C07K 14/475* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2004/0081984 A1* | 4/2004 | Laurie et al. ............... 435/6 |
| 2007/0207522 A1 | 9/2007 | Laurie et al. | |
| 2009/0280190 A1 | 11/2009 | Folkman et al. | |
| 2010/0233095 A1 | 9/2010 | Duan et al. | |
| 2010/0233242 A1 | 9/2010 | Tirrell et al. | |
| 2011/0039776 A1 | 2/2011 | Chilkoti | |

FOREIGN PATENT DOCUMENTS

WO    2013016578 A2    1/2013

OTHER PUBLICATIONS

MacEwan et al., Elastin-Like Polypeptides: Biomedical Applications of Tunable Biopolymers, Jan. 20, 2010, Peptide Science 94(1):60-77.*
Samudre et al., Lacritin, a Novel Human Tear Glycoprotein, Promotes Sustained Basal Tearing and Is Well Tolerated, Aug. 2011, Investigative Ophthalmology & Visual Science 52(9):6265-6270.*
PCT/US2012/048404 International Search Report dated Jan. 22, 2013.
PCT/US2012/048404 Written Opinion dated Jan. 22, 2013.
Floss et al. Elastin-like polypeptides revolutionize recombinant protein expression and their biomedical application. Trends in Biotechnology (2010). 28(1): 37-45.
Shamji et al. Treatment of neuroinflammation by soluble tumor necrosis factor receptor Type II fused to a thermally responsive carrier: Laboratory Investifgation. J Neurosurg Spine (2008). 9(2):221-228.

* cited by examiner

*Primary Examiner* — John Ulm
(74) *Attorney, Agent, or Firm* — Stephen W. Chen; Nixon Peabody LLP

(57) ABSTRACT

Described herein are bioresponsive protein polymers for therapeutic applications, including delivery to physiologically demanding environments, such as the eye surface. Bioresponsive protein polymers can be fused with biopharmaceuticals using genetic engineering techniques for enhanced therapeutic activity. In certain embodiments, the unique temperature-sensitive phase separation properties of bioresponsive protein polymers, allows generation of therapeutics resistant to ocular clearance. Such fusion proteins containing bioresponsive protein polymers and biopharmaceuticals allow retention of drugs in the eye for much longer periods of time. Improved biostability and bioavailability improves drug efficacy, while reducing cost and eliminating the need for repeated drug Application.

15 Claims, 23 Drawing Sheets

Figure 1
A)
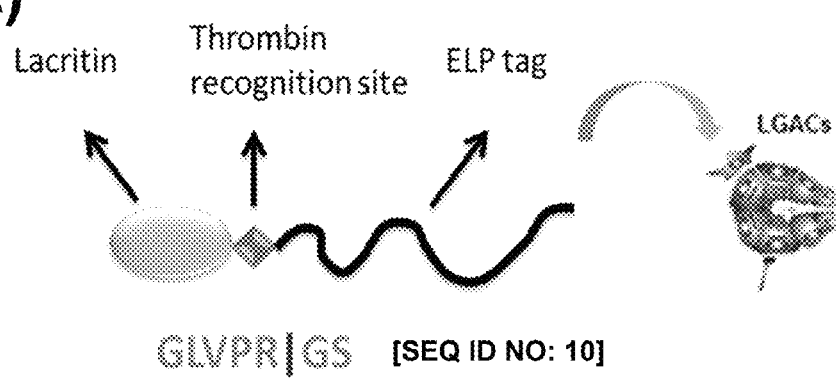
GLVPR|GS [SEQ ID NO: 10]
B) 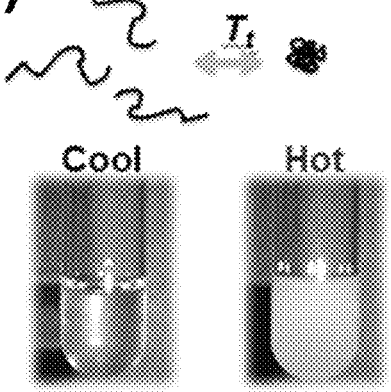
C) 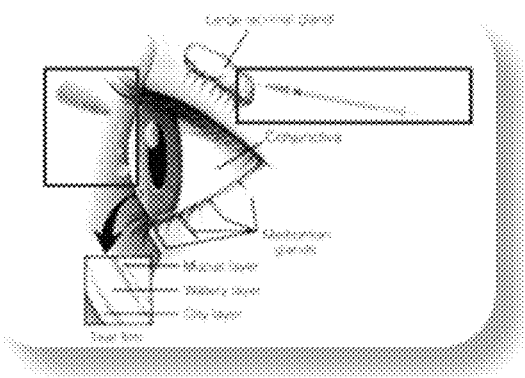

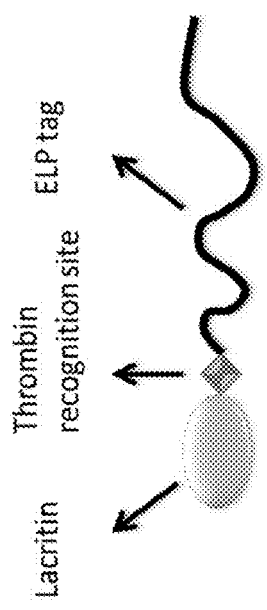

Lacritin — Thrombin recognition site — ELP tag

B

GLVPR|GS [SEQ ID NO: 10]

Hydrophobicity

| Name | I96 | Lac-I96 | V96 | Lac-V96 | S96 | Lac-S96 | S48I48 | Lac-S48I48 | Lacritin |
|---|---|---|---|---|---|---|---|---|---|
| | [SEQ ID NO: 11] | [SEQ ID NO: 14] | [SEQ ID NO: 17] | [SEQ ID NO: 14] | [SEQ ID NO: 12] | [SEQ ID NO: 16] | [SEQ ID NO: 13] | [SEQ ID NO: 18] | [SEQ ID NO: 4] |
| Sequence | G(VPGIG)96 | Lac-Thrombin-G(VPGIG)96 | G(VPGVG)96 | Lac-Thrombin-G(VPGVG)96 | G(VPGSG)96 | Lac-Thrombin-G(VPGSG)96 | G(VPGSG)48(VPGIG)48 | Lac-Thrombin-G(VPGSG)48(VPGIG)48 | Lac |
| m/z | 40.9 | 53.9 | 39.6 | 52.5 | 38.4 | 51.4 | 39.7 | 52.5 | 12.9 |
| [M+H]+ | 39.2 | 53.1 | 39.2 | 52.3 | 38.9 | 51.1 | 39.5 | 52.2 | 12.7 |
| 25μM T_t (°C) | 19.5 | 14.5 | 31.6 | 26.8 | 57.6 | NA | 26.6 / 75.0 | 18.7 | NA |

Micelle — Monomer

Figure 3
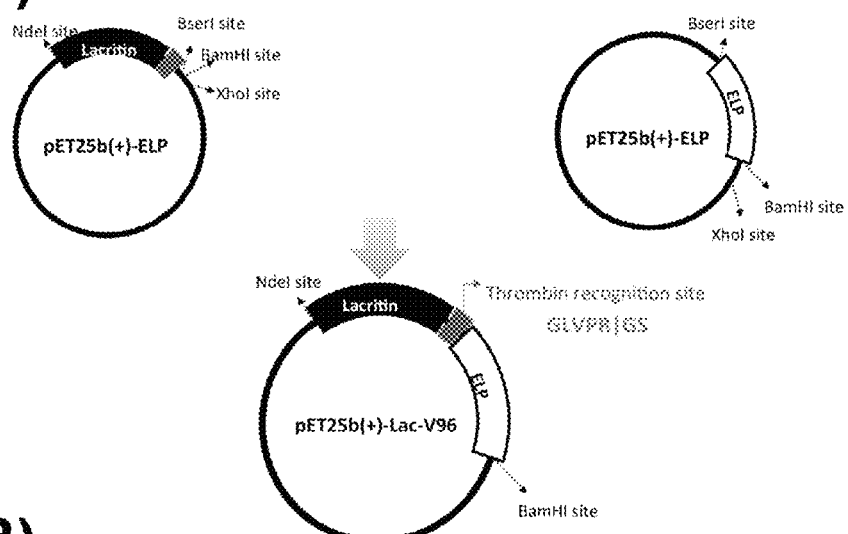
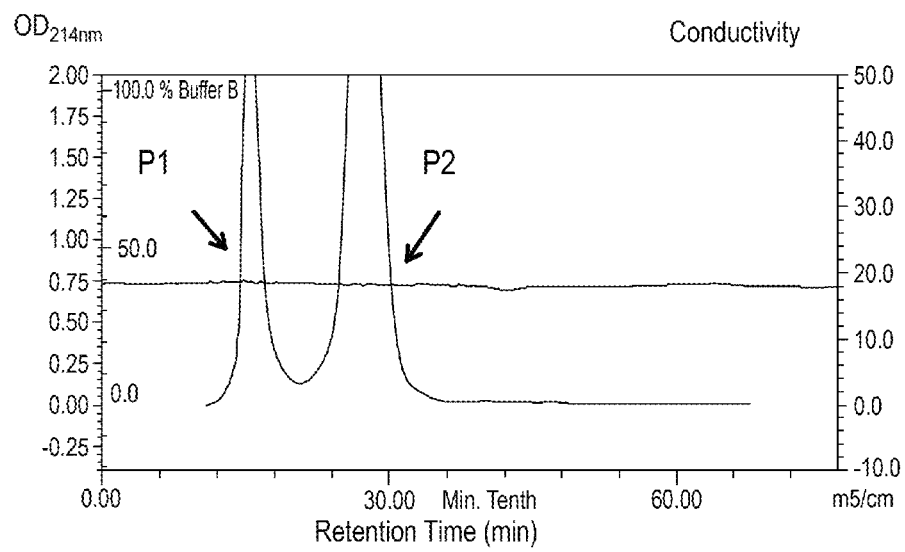

Figure 4
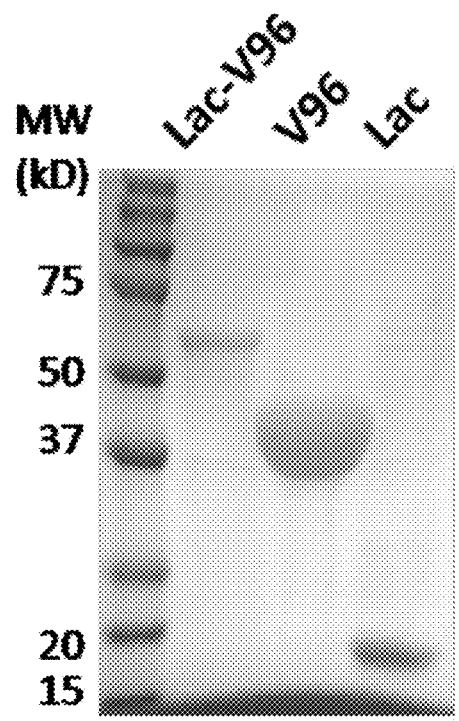
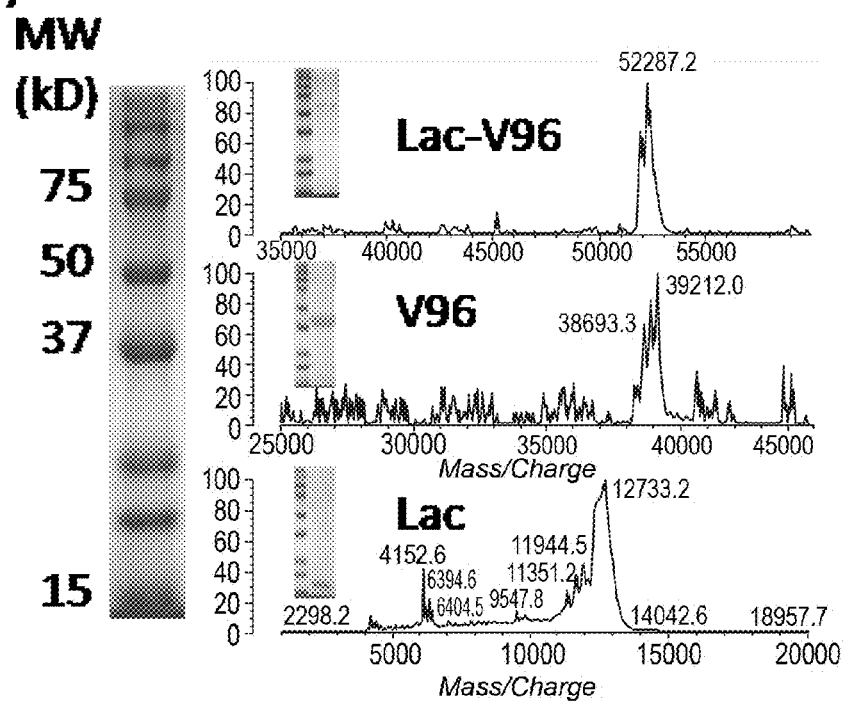

Figure 5
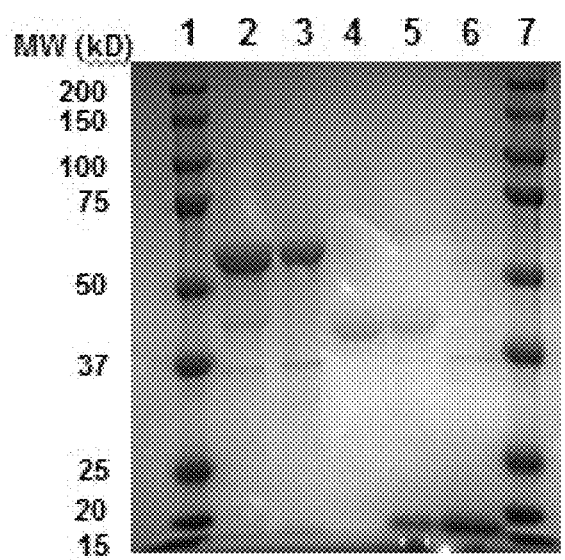
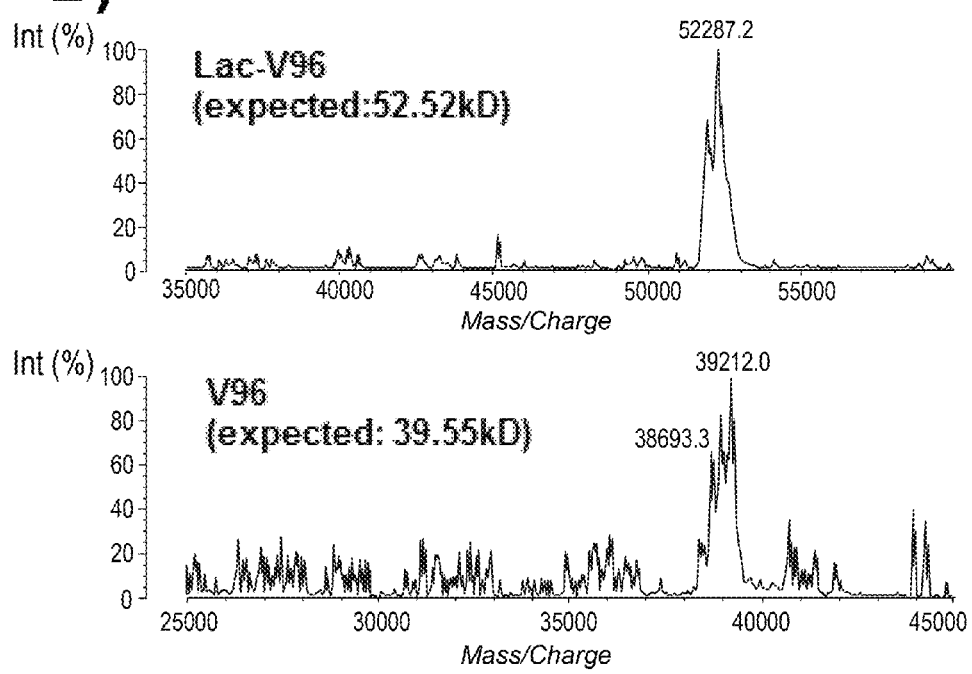

Figure 6
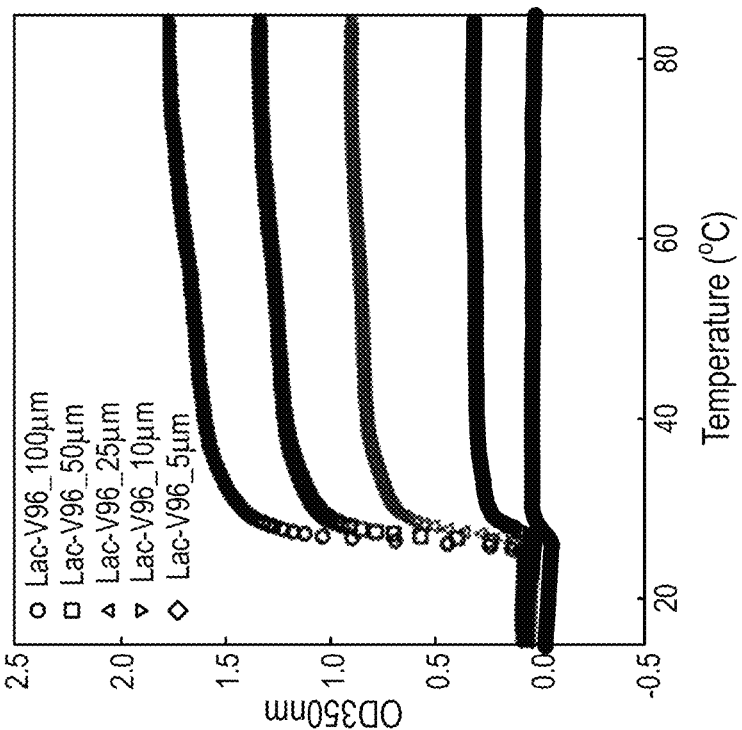
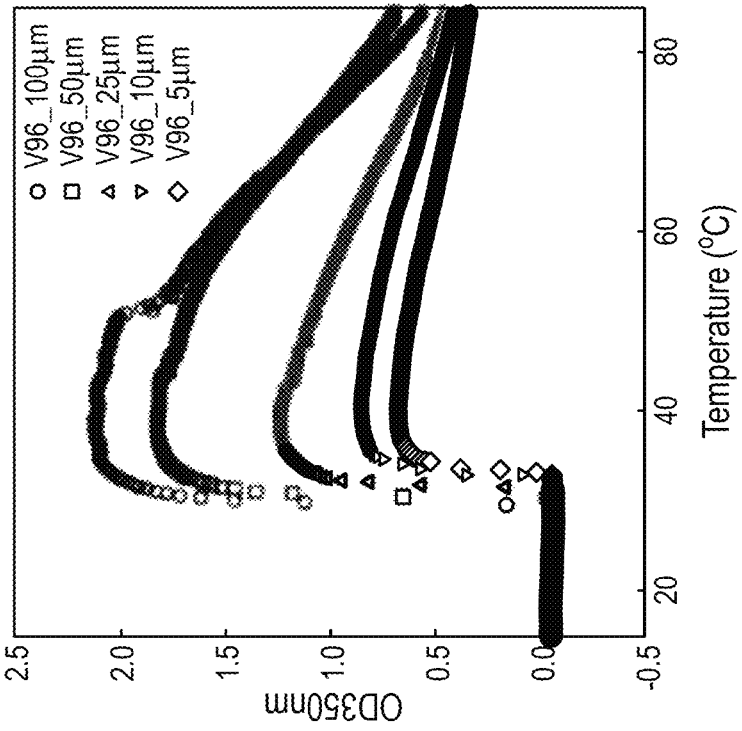

Figure 6
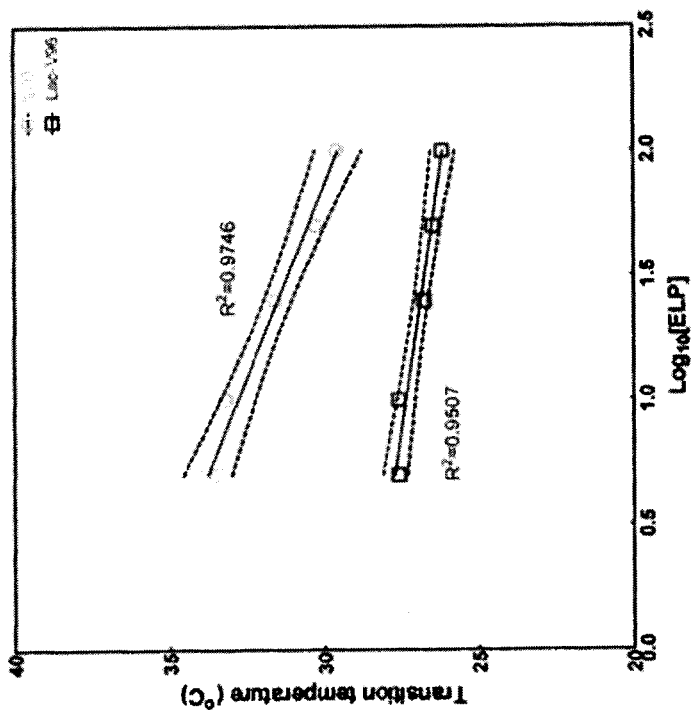
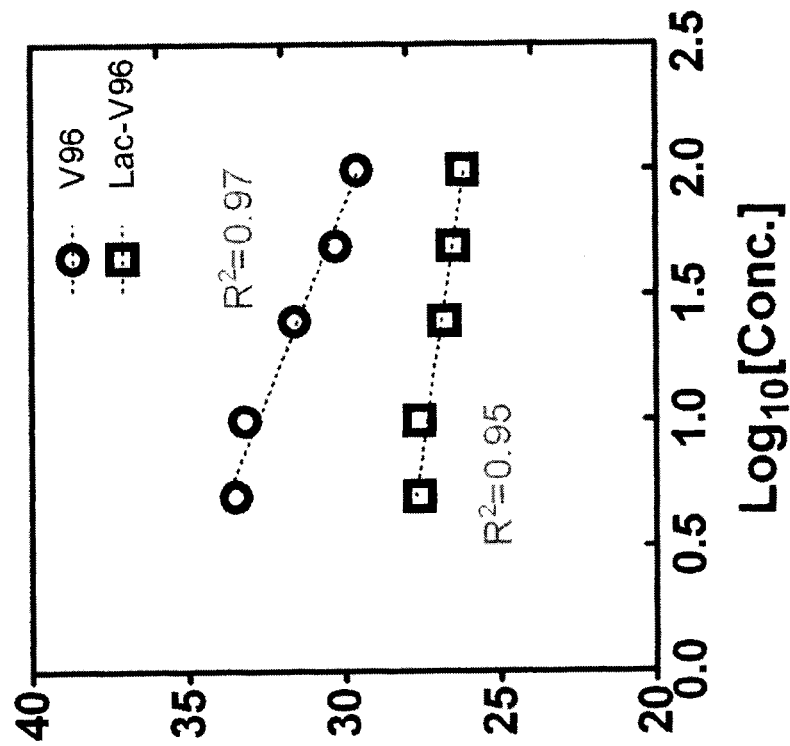

Figure 7
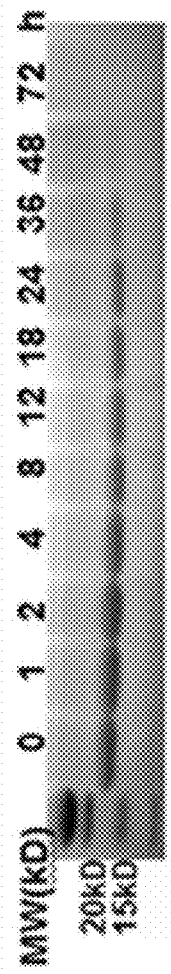
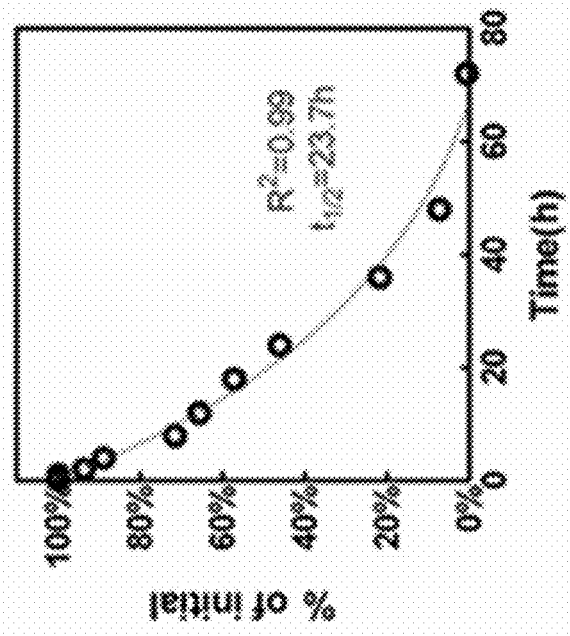
A)
B) GEDASSDSTGADPAQEAGTSK(P)NEEISGPAEPASPPETTTAQETSAAAVQGTAKVTS
SRQELNPLKSIVEKSILLTEQALAKAGKGMHGGVPGGK(Q)FIENG SEFAQKLLLKKFSLL
KPWAGLLVPRGSG(VPGVG)₆₀Y    [SEQ ID NO: 4]

Figure 9
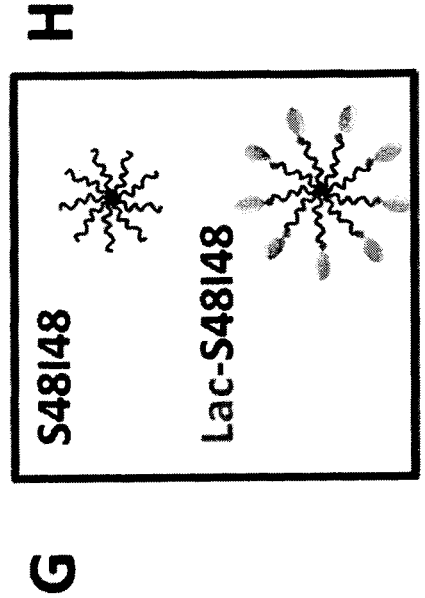
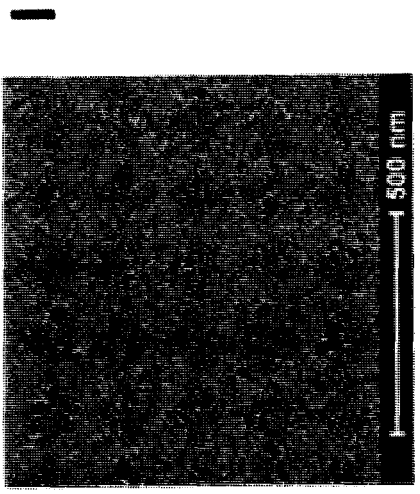
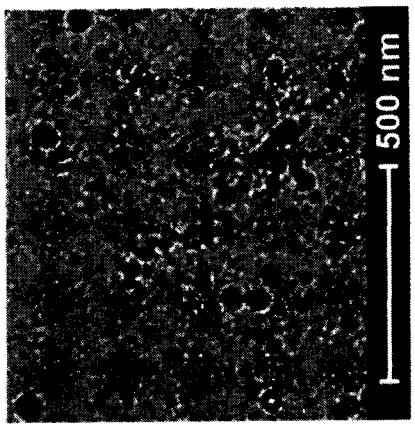

Figure 11
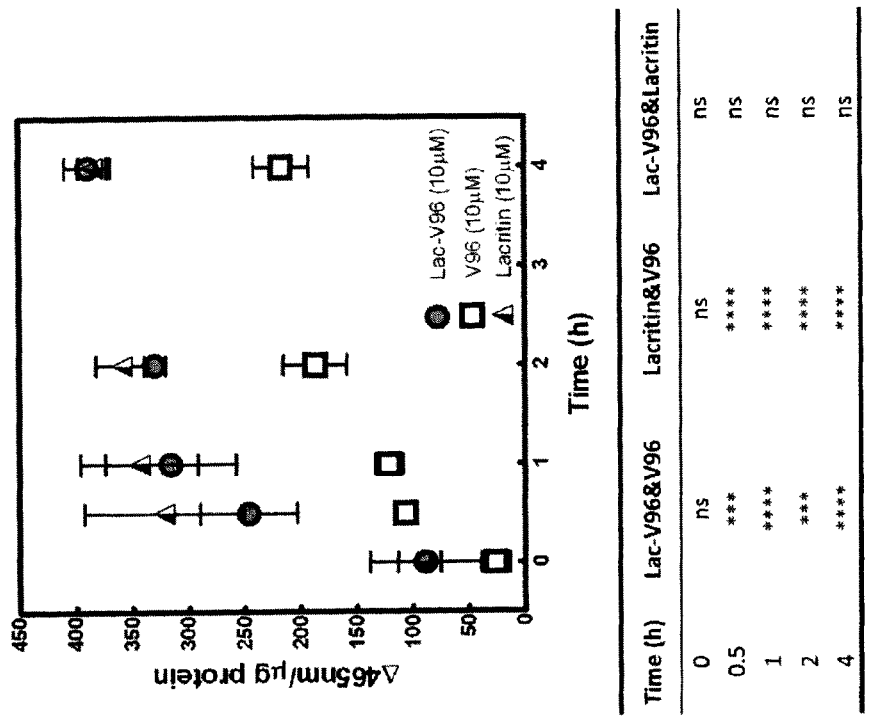
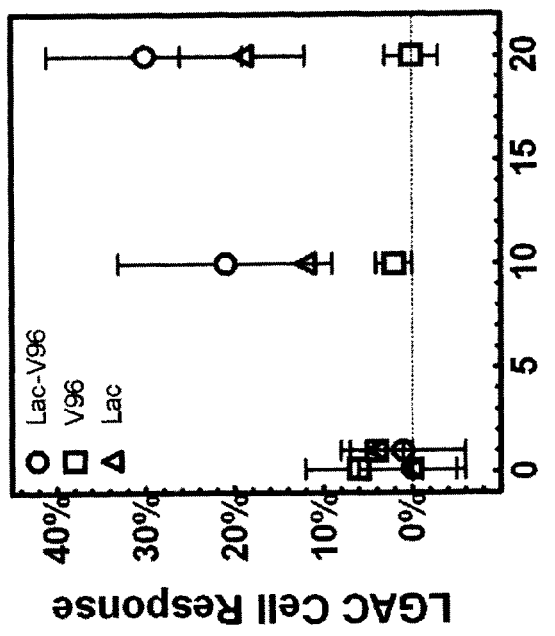

Figure 13
A)
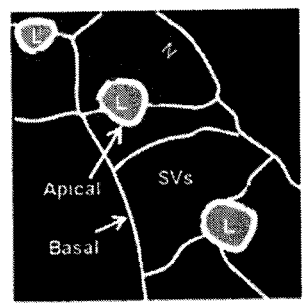
B)
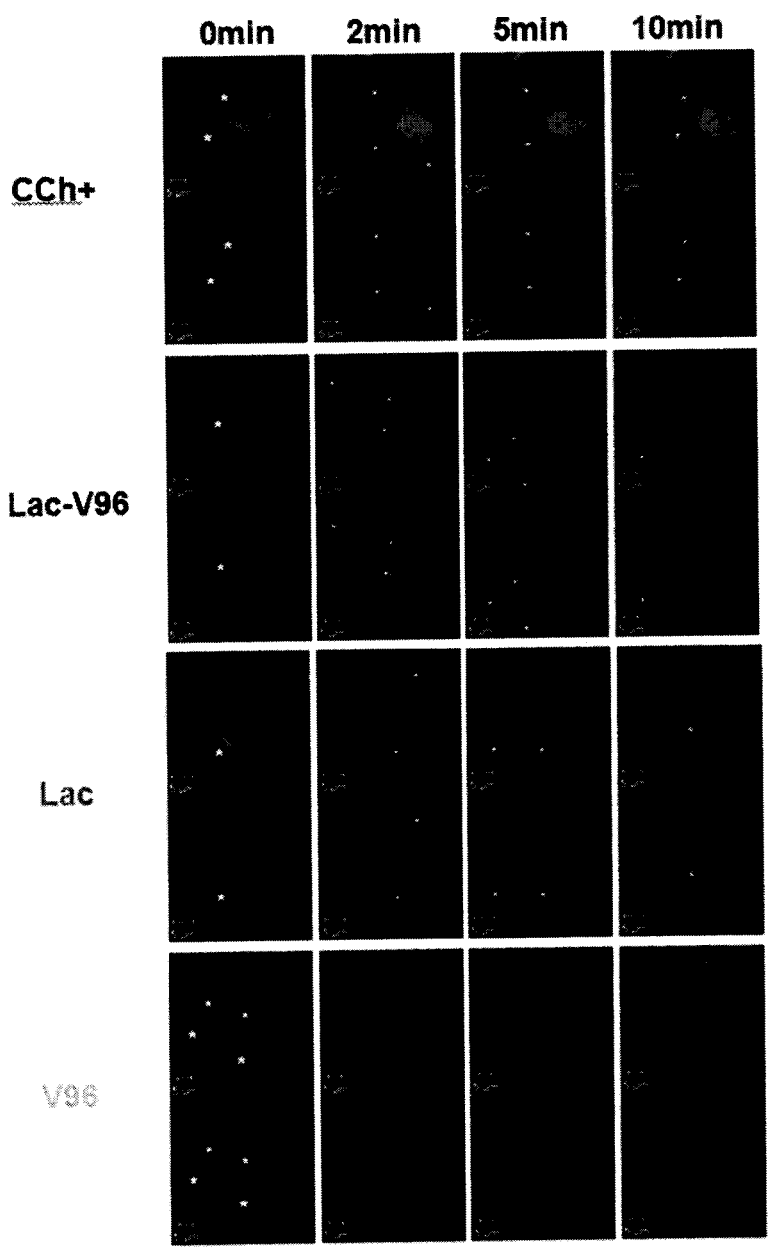

| | Sequence | m/z | [M+H]⁺ |
|---|---|---|---|
| 1 | MGEDASSDSTGADPAQEAGTSKPNEEISGPAEPASPPETTTTAQETSAAA<br>VQGTAKVTSSRQELNPLKSIVEKSILLTEQALAK AGKGMHGGVPGGKQFIE<br>NGSEFAQKLLKFSLLKPWAQLVRR| [SEQ ID NO: 21] | 12.97 | 12.96 |
| 2 | MGEDASSDSTGADPAQEAGTSKPNEEISGPAEPASPPETTTTAQETSAAA<br>VQGTAKVTSSRQELNPLKSIVEKSILLTEQALAK AGKGMHGGVPGGKQFIE<br>NGSEFAQKLLKFSLL|K| [SEQ ID NO: 22] | 11.97/<br>12.09 | 12.00 |
| 3 | MGEDASSDSTGADPAQEAGTSKPNEEISGPAEPASPPETTTTAQETSAAA<br>VQGTAKVTSSRQELNPLKSIVEKSILLTEQALAK AGKGMHGGVPGGKQFIE<br>NGSEFAQKLLL|K| [SEQ ID NO: 23] | 11.38/<br>11.51 | 11.35/<br>11.47/<br>11.50 |
| 4 | |PNEEISGPAEPASPPETTTTAQETSAAAVQGTAKVTSSRQELNPLKSIVEK<br>SILLTEQALAK| [SEQ ID NO: 24] | 6.42 | 6.36 |

```
                              SEQUENCE LISTING

<160> NUMBER OF SEQ ID NOS: 24

<210> SEQ ID NO 1
<211> LENGTH: 406
<212> TYPE: DNA
<213> ORGANISM: Homo sapiens

<400> SEQUENCE: 1
catatggaag acgcttcttc tgactctacc ggtgctgacc cggctcagga agctggtacc      60
tctaaaccga acgaagaaat ctctggtccg gctgaaccgg cttctccgcc ggaaaccacc     120
accaccgctc aggaaacctc tgctgctgct gttcagggta ccgctaaagt tacctcttct     180
cgtcaggaac tgaacccgct gaaatctatc gttgaaaaat ctatcctgct gaccgaacag     240
gctctggcta aagctggtaa aggtatgcac ggtggtgttc cgggtggtaa acagttcatc     300
gaaaacggtt ctgaattcgc tcagaaactg ctgaaaaaat ctctctgct gaaaccgtgg      360 gctggtctgg ttccgcgtgg ttctggttac tgatctcctc ggatcc                    406

<210> SEQ ID NO 2
<211> LENGTH: 508
<212> TYPE: DNA
<213> ORGANISM: Homo sapiens

<400> SEQUENCE: 2
gcagattctg tggttatact cactcctcat cccaaagaat gaaatttacc actctcctct      60
tcttggcagc tgtagcaggg gccctggtct atgctgaaga tgcctcctct gactcgacgg     120
gtgctgatcc tgcccaggaa gctgggacct ctaagcctaa tgaagagatc tcaggtccag     180
cagaaccagc ttcaccccca gagacaacca caacagccca ggagacttcg gcggcagcag     240
ttcaggggac agccaaggtc acctcaagca ggcaggaact aaaccccctg aaatccatag     300
tggagaaaag tatcttacta acagaacaag cccttgcaaa agcaggaaaa ggaatgcacg     360
gaggcgtgcc aggtggaaaa caattcatcg aaaatgaag tgaatttgca caaaaattac      420
tgaagaaatt cagtctatta aaaccatggg catgagaagc tgaaaagaat gggatcattg     480
gacttaaagc cttaaatacc cttgtagc                                        508

<210> SEQ ID NO 3
<211> LENGTH: 138
<212> TYPE: PRT
<213> ORGANISM: Homo sapiens

<400> SEQUENCE: 3

Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Thr Ala Gln Glu Thr Ser
    50                  55                  60

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
```

```
            85                 90                 95
Gln Ala Leu Ala Lys Ala Gly Lys Gly Met His Gly Val Pro Gly
                100                105                110

Gly Lys Gln Phe Ile Glu Asn Gly Ser Glu Phe Ala Gln Lys Leu Leu
            115                120                125

Lys Lys Phe Ser Leu Leu Lys Pro Trp Ala
        130                135
```

<210> SEQ ID NO 4
<211> LENGTH: 118
<212> TYPE: PRT
<213> ORGANISM: Homo sapiens

<400> SEQUENCE: 4

```
Asp Ala Ser Ser Asp Ser Thr Gly Ala Asp Pro Ala Gln Glu Ala Gly
1               5                   10                  15

Thr Ser Lys Pro Asn Glu Glu Ile Ser Gly Pro Ala Glu Pro Ala Ser
            20                  25                  30

Pro Pro Glu Thr Thr Thr Thr Ala Gln Glu Thr Ser Ala Ala Ala Val
        35                  40                  45

Gln Gly Thr Ala Lys Val Thr Ser Ser Arg Gln Glu Leu Asn Pro Leu
    50                  55                  60
Lys Ser Ile Val Glu Lys Ser Ile Leu Leu Thr Glu Gln Ala Leu Ala
65                  70                  75                  80

Lys Ala Gly Lys Gly Met His Gly Val Pro Gly Gly Lys Gln Phe
                85                  90                  95

Ile Glu Asn Gly Ser Glu Phe Ala Gln Lys Leu Leu Lys Phe Ser
            100                 105                 110

Leu Leu Lys Pro Trp Ala
        115
```

<210> SEQ ID NO 5
<211> LENGTH: 120
<212> TYPE: PRT
<213> ORGANISM: Homo sapiens

<400> SEQUENCE: 5

```
Met Glu Asp Ala Ser Ser Asp Ser Thr Gly Ala Asp Pro Ala Gln Glu
1               5                   10                  15

Ala Gly Thr Ser Lys Pro Asn Glu Glu Ile Ser Gly Pro Ala Glu Pro
            20                  25                  30

Ala Ser Pro Pro Glu Thr Thr Thr Thr Ala Gln Glu Thr Ser Ala Ala
        35                  40                  45

Ala Val Gln Gly Thr Ala Lys Val Thr Ser Ser Arg Gln Glu Leu Asn
    50                  55                  60

Pro Leu Lys Ser Ile Val Glu Lys Ser Ile Leu Leu Thr Glu Gln Ala
65                  70                  75                  80

Leu Ala Lys Ala Gly Lys Gly Met His Gly Val Pro Gly Gly Lys
                85                  90                  95

Gln Phe Ile Glu Asn Gly Ser Glu Phe Ala Gln Lys Leu Leu Lys Lys
            100                 105                 110

Phe Ser Leu Leu Lys Pro Trp Ala
        115                 120
```

<210> SEQ ID NO 6
<211> LENGTH: 121
<212> TYPE: PRT

<213> ORGANISM: Homo sapiens

<400> SEQUENCE: 6

Met Gly Glu Asp Ala Ser Ser Asp Ser Thr Gly Ala Asp Pro Ala Gln
1               5                   10                  15

Glu Ala Gly Thr Ser Lys Pro Asn Glu Glu Ile Ser Gly Pro Ala Glu
            20                  25                  30

Pro Ala Ser Pro Pro Glu Thr Thr Thr Ala Gln Glu Thr Ser Ala
        35                  40                  45

Ala Ala Val Gln Gly Thr Ala Lys Val Thr Ser Ser Arg Gln Glu Leu
    50                  55                  60

Asn Pro Leu Lys Ser Ile Val Glu Lys Ser Ile Leu Leu Thr Glu Gln
65                  70                  75                  80

Ala Leu Ala Lys Ala Gly Lys Gly Met His Gly Gly Val Pro Gly Gly
                85                  90                  95

Lys Gln Phe Ile Glu Asn Gly Ser Glu Phe Ala Gln Lys Leu Leu Lys
            100                 105                 110

Lys Phe Ser Leu Leu Lys Pro Trp Ala
            115                 120

<210> SEQ ID NO 7
<211> LENGTH: 117
<212> TYPE: PRT
<213> ORGANISM: Homo sapiens

<400> SEQUENCE: 7

Met Gly Glu Asp Ala Ser Ser Asp Ser Thr Gly Ala Asp Pro Ala Gln
1               5                   10                  15

Glu Ala Gly Thr Ser Lys Pro Asn Glu Glu Ile Ser Gly Pro Ala Glu
            20                  25                  30

Pro Ala Ser Pro Pro Glu Thr Thr Thr Ala Gln Glu Thr Ser Ala
        35                  40                  45

Ala Ala Val Gln Gly Thr Ala Lys Val Thr Ser Ser Arg Gln Glu Leu
    50                  55                  60

Asn Pro Leu Lys Ser Ile Val Glu Lys Ser Ile Leu Leu Thr Glu Gln
65                  70                  75                  80

Ala Leu Ala Lys Ala Gly Lys Gly Met His Gly Gly Val Pro Gly Gly
                85                  90                  95

Lys Gln Phe Ile Glu Asn Gly Ser Glu Phe Ala Gln Lys Leu Leu Lys
            100                 105                 110

Lys Phe Ser Leu Leu
            115

<210> SEQ ID NO 8
<211> LENGTH: 112
<212> TYPE: PRT
<213> ORGANISM: Homo sapiens

<400> SEQUENCE: 8

Met Gly Glu Asp Ala Ser Ser Asp Ser Thr Gly Ala Asp Pro Ala Gln
1               5                   10                  15

Glu Ala Gly Thr Ser Lys Pro Asn Glu Glu Ile Ser Gly Pro Ala Glu
            20                  25                  30

Pro Ala Ser Pro Pro Glu Thr Thr Thr Ala Gln Glu Thr Ser Ala
        35                  40                  45

Ala Ala Val Gln Gly Thr Ala Lys Val Thr Ser Ser Arg Gln Glu Leu
    50                  55                  60

Asn Pro Leu Lys Ser Ile Val Glu Lys Ser Ile Leu Leu Thr Glu Gln
65                  70                  75                  80

Ala Leu Ala Lys Ala Gly Lys Gly Met His Gly Gly Val Pro Gly Gly
                85                  90                  95

Lys Gln Phe Ile Glu Asn Gly Ser Glu Phe Ala Gln Lys Leu Leu Lys
            100                 105                 110

<210> SEQ ID NO 9
<211> LENGTH: 8
<212> TYPE: PRT
<213> ORGANISM: Homo sapiens

<400> SEQUENCE: 9

Gly Leu Val Pro Arg Gly Ser Gly
1               5

<210> SEQ ID NO 10
<211> LENGTH: 7
<212> TYPE: PRT
<213> ORGANISM: Artificial Sequence
<220> FEATURE:
<223> OTHER INFORMATION: THROMBIN RECOGNITION SITE

<400> SEQUENCE: 10

Gly Leu Val Pro Arg Gly Ser
1               5

<210> SEQ ID NO 11
<211> LENGTH: 482
<212> TYPE: PRT
<213> ORGANISM: Artificial Sequence
<220> FEATURE:
<223> OTHER INFORMATION: I96 SEQUENCE

<400> SEQUENCE: 11

Gly Val Pro Gly Ile Gly Val Pro Gly Ile Gly Val Pro Gly Ile Gly
1               5                   10                  15

Val Pro Gly Ile Gly Val Pro Gly Ile Gly Val Pro Gly Ile Gly Val
                20                  25                  30

Pro Gly Ile Gly Val Pro Gly Ile Gly Val Pro Gly Ile Gly Val Pro
            35                  40                  45

Gly Ile Gly Val Pro Gly Ile Gly Val Pro Gly Ile Gly Val Pro Gly
        50                  55                  60

Ile Gly Val Pro Gly Ile Gly Val Pro Gly Ile Gly Val Pro Gly Ile
65                  70                  75                  80

Gly Val Pro Gly Ile Gly Val Pro Gly Ile Gly Val Pro Gly Ile Gly
                85                  90                  95

Val Pro Gly Ile Gly Val Pro Gly Ile Gly Val Pro Gly Ile Gly Val
            100                 105                 110

Pro Gly Ile Gly Val Pro Gly Ile Gly Val Pro Gly Ile Gly Val Pro
        115                 120                 125

Gly Ile Gly Val Pro Gly Ile Gly Val Pro Gly Ile Gly Val Pro Gly
    130                 135                 140

Ile Gly Val Pro Gly Ile Gly Val Pro Gly Ile Gly Val Pro Gly Ile
145                 150                 155                 160

Gly Val Pro Gly Ile Gly Val Pro Gly Ile Gly Val Pro Gly Ile Gly
                165                 170                 175

Val Pro Gly Ile Gly Val Pro Gly Ile Gly Val Pro Gly Ile Gly Val
            180                 185                 190

Pro Gly Ile Gly Val Pro Gly Ile Gly Val Pro Gly Ile Gly Val Pro
          195                 200                 205

Gly Ile Gly Val Pro Gly Ile Gly Val Pro Gly Ile Gly Val Pro Gly
    210                 215                 220

Ile Gly Val Pro Gly Ile Gly Val Pro Gly Ile Gly Val Pro Gly Ile
225                 230                 235                 240

Gly Val Pro Gly Ile Gly Val Pro Gly Ile Gly Val Pro Gly Ile Gly
            245                 250                 255

Val Pro Gly Ile Gly Val Pro Gly Ile Gly Val Pro Gly Ile Gly Val
        260                 265                 270

Pro Gly Ile Gly Val Pro Gly Ile Gly Val Pro Gly Ile Gly Val Pro
    275                 280                 285

Gly Ile Gly Val Pro Gly Ile Gly Val Pro Gly Ile Gly Val Pro Gly
    290                 295                 300

Ile Gly Val Pro Gly Ile Gly Val Pro Gly Ile Gly Val Pro Gly Ile
305                 310                 315                 320

Gly Val Pro Gly Ile Gly Val Pro Gly Ile Gly Val Pro Gly Ile Gly
            325                 330                 335

Val Pro Gly Ile Gly Val Pro Gly Ile Gly Val Pro Gly Ile Gly Val
        340                 345                 350

Pro Gly Ile Gly Val Pro Gly Ile Gly Val Pro Gly Ile Gly Val Pro
    355                 360                 365

Gly Ile Gly Val Pro Gly Ile Gly Val Pro Gly Ile Gly Val Pro Gly
    370                 375                 380

Ile Gly Val Pro Gly Ile Gly Val Pro Gly Ile Gly Val Pro Gly Ile
385                 390                 395                 400

Gly Val Pro Gly Ile Gly Val Pro Gly Ile Gly Val Pro Gly Ile Gly
            405                 410                 415

Val Pro Gly Ile Gly Val Pro Gly Ile Gly Val Pro Gly Ile Gly Val
        420                 425                 430

Pro Gly Ile Gly Val Pro Gly Ile Gly Val Pro Gly Ile Gly Val Pro
    435                 440                 445

Gly Ile Gly Val Pro Gly Ile Gly Val Pro Gly Ile Gly Val Pro Gly
    450                 455                 460

Ile Gly Val Pro Gly Ile Gly Val Pro Gly Ile Gly Val Pro Gly Ile
465                 470                 475                 480

Gly Tyr

<210> SEQ ID NO 12
<211> LENGTH: 482
<212> TYPE: PRT
<213> ORGANISM: Artificial Sequence
<220> FEATURE:
<223> OTHER INFORMATION: S96 SEQUENCE

<400> SEQUENCE: 12

Gly Val Pro Gly Ser Gly Val Pro Gly Ser Gly Val Pro Gly Ser Gly
1               5                   10                  15

Val Pro Gly Ser Gly Val Pro Gly Ser Gly Val Pro Gly Ser Gly Val
            20                  25                  30

Pro Gly Ser Gly Val Pro Gly Ser Gly Val Pro Gly Ser Gly Val Pro
        35                  40                  45

Gly Ser Gly Val Pro Gly Ser Gly Val Pro Gly Ser Gly Val Pro Gly
    50                  55                  60

-continued

Ser Gly Val Pro Gly Ser Gly Val Pro Gly Ser Gly Val Pro Gly Ser
65                  70                  75                  80

Gly Val Pro Gly Ser Gly Val Pro Gly Ser Gly Val Pro Gly Ser Gly
                85                  90                  95

Val Pro Gly Ser Gly Val Pro Gly Ser Gly Val Pro Gly Ser Gly Val
            100                 105                 110

Pro Gly Ser Gly Val Pro Gly Ser Gly Val Pro Gly Ser Gly Val Pro
        115                 120                 125

Gly Ser Gly Val Pro Gly Ser Gly Val Pro Gly Ser Gly Val Pro Gly
130                 135                 140

Ser Gly Val Pro Gly Ser Gly Val Pro Gly Ser Gly Val Pro Gly Ser
145                 150                 155                 160

Gly Val Pro Gly Ser Gly Val Pro Gly Ser Gly Val Pro Gly Ser Gly
                165                 170                 175

Val Pro Gly Ser Gly Val Pro Gly Ser Gly Val Pro Gly Ser Gly Val
            180                 185                 190

Pro Gly Ser Gly Val Pro Gly Ser Gly Val Pro Gly Ser Gly Val Pro
        195                 200                 205

Gly Ser Gly Val Pro Gly Ser Gly Val Pro Gly Ser Gly Val Pro Gly
210                 215                 220

Ser Gly Val Pro Gly Ser Gly Val Pro Gly Ser Gly Val Pro Gly Ser
225                 230                 235                 240

Gly Val Pro Gly Ser Gly Val Pro Gly Ser Gly Val Pro Gly Ser Gly
                245                 250                 255

Val Pro Gly Ser Gly Val Pro Gly Ser Gly Val Pro Gly Ser Gly Val
            260                 265                 270

Pro Gly Ser Gly Val Pro Gly Ser Gly Val Pro Gly Ser Gly Val Pro
        275                 280                 285

Gly Ser Gly Val Pro Gly Ser Gly Val Pro Gly Ser Gly Val Pro Gly
290                 295                 300

Ser Gly Val Pro Gly Ser Gly Val Pro Gly Ser Gly Val Pro Gly Ser
305                 310                 315                 320

Gly Val Pro Gly Ser Gly Val Pro Gly Ser Gly Val Pro Gly Ser Gly
                325                 330                 335

Val Pro Gly Ser Gly Val Pro Gly Ser Gly Val Pro Gly Ser Gly Val
            340                 345                 350

Pro Gly Ser Gly Val Pro Gly Ser Gly Val Pro Gly Ser Gly Val Pro
        355                 360                 365

Gly Ser Gly Val Pro Gly Ser Gly Val Pro Gly Ser Gly Val Pro Gly
370                 375                 380

Ser Gly Val Pro Gly Ser Gly Val Pro Gly Ser Gly Val Pro Gly Ser
385                 390                 395                 400

Gly Val Pro Gly Ser Gly Val Pro Gly Ser Gly Val Pro Gly Ser Gly
                405                 410                 415

Val Pro Gly Ser Gly Val Pro Gly Ser Gly Val Pro Gly Ser Gly Val
            420                 425                 430

Pro Gly Ser Gly Val Pro Gly Ser Gly Val Pro Gly Ser Gly Val Pro
        435                 440                 445

Gly Ser Gly Val Pro Gly Ser Gly Val Pro Gly Ser Gly Val Pro Gly
    450                 455                 460

Ser Gly Val Pro Gly Ser Gly Val Pro Gly Ser Gly Val Pro Gly Ser
465                 470                 475                 480

Gly Tyr

<210> SEQ ID NO 13
<211> LENGTH: 482
<212> TYPE: PRT
<213> ORGANISM: Artificial Sequence
<220> FEATURE:
<223> OTHER INFORMATION: S48I48 SEQUENCE

<400> SEQUENCE: 13

```
Gly Val Pro Gly Ser Gly Val Pro Gly Ser Gly Val Pro Gly Ser Gly
1               5                   10                  15

Val Pro Gly Ser Gly Val Pro Gly Ser Gly Val Pro Gly Ser Gly Val
            20                  25                  30

Pro Gly Ser Gly Val Pro Gly Ser Gly Val Pro Gly Ser Gly Val Pro
        35                  40                  45

Gly Ser Gly Val Pro Gly Ser Gly Val Pro Gly Ser Gly Val Pro Gly
    50                  55                  60

Ser Gly Val Pro Gly Ser Gly Val Pro Gly Ser Gly Val Pro Gly Ser
65                  70                  75                  80

Gly Val Pro Gly Ser Gly Val Pro Gly Ser Gly Val Pro Gly Ser Gly
                85                  90                  95

Val Pro Gly Ser Gly Val Pro Gly Ser Gly Val Pro Gly Ser Gly Val
            100                 105                 110

Pro Gly Ser Gly Val Pro Gly Ser Gly Val Pro Gly Ser Gly Val Pro
        115                 120                 125

Gly Ser Gly Val Pro Gly Ser Gly Val Pro Gly Ser Gly Val Pro Gly
    130                 135                 140

Ser Gly Val Pro Gly Ser Gly Val Pro Gly Ser Gly Val Pro Gly Ser
145                 150                 155                 160

Gly Val Pro Gly Ser Gly Val Pro Gly Ser Gly Val Pro Gly Ser Gly
                165                 170                 175

Val Pro Gly Ser Gly Val Pro Gly Ser Gly Val Pro Gly Ser Gly Val
            180                 185                 190

Pro Gly Ser Gly Val Pro Gly Ser Gly Val Pro Gly Ser Gly Val Pro
        195                 200                 205

Gly Ser Gly Val Pro Gly Ser Gly Val Pro Gly Ser Gly Val Pro Gly
    210                 215                 220

Ser Gly Val Pro Gly Ser Gly Val Pro Gly Ser Gly Val Pro Gly Ser
225                 230                 235                 240

Gly Val Pro Gly Ile Gly Val Pro Gly Ile Gly Val Pro Gly Ile Gly
                245                 250                 255

Val Pro Gly Ile Gly Val Pro Gly Ile Gly Val Pro Gly Ile Gly Val
            260                 265                 270

Pro Gly Ile Gly Val Pro Gly Ile Gly Val Pro Gly Ile Gly Val Pro
        275                 280                 285

Gly Ile Gly Val Pro Gly Ile Gly Val Pro Gly Ile Gly Val Pro Gly
    290                 295                 300

Ile Gly Val Pro Gly Ile Gly Val Pro Gly Ile Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Ile Gly Val Pro Gly Ile Gly Val
            340                 345                 350

Pro Gly Ile Gly Val Pro Gly Ile Gly Val Pro Gly Ile Gly Val Pro
        355                 360                 365
```

Gly Ile Gly Val Pro Gly Ile Gly Val Pro Gly Ile Gly Val Pro Gly
            370                 375                 380

Ile Gly Val Pro Gly Ile Gly Val Pro Gly Ile Gly Val Pro Gly Ile
385                 390                 395                 400

Gly Val Pro Gly Ile Gly Val Pro Gly Ile Gly Val Pro Gly Ile Gly
            405                 410                 415

Val Pro Gly Ile Gly Val Pro Gly Ile Gly Val Pro Gly Ile Gly Val
            420                 425                 430

Pro Gly Ile Gly Val Pro Gly Ile Gly Val Pro Gly Ile Gly Val Pro
            435                 440                 445

Gly Ile Gly Val Pro Gly Ile Gly Val Pro Gly Ile Gly Val Pro Gly
            450                 455                 460

Ile Gly Val Pro Gly Ile Gly Val Pro Gly Ile Gly Val Pro Gly Ile
465                 470                 475                 480

Gly Tyr

<210> SEQ ID NO 14
<211> LENGTH: 609
<212> TYPE: PRT
<213> ORGANISM: Artificial Sequence
<220> FEATURE:
<223> OTHER INFORMATION: LAC-V96

<400> SEQUENCE: 14

Met Glu Asp Ala Ser Ser Asp Ser Thr Gly Ala Asp Pro Ala Gln Glu
1               5                   10                  15

Ala Gly Thr Ser Lys Pro Asn Glu Glu Ile Ser Gly Pro Ala Glu Pro
            20                  25                  30

Ala Ser Pro Pro Glu Thr Thr Thr Thr Ala Gln Glu Thr Ser Ala Ala
            35                  40                  45

Ala Val Gln Gly Thr Ala Lys Val Thr Ser Ser Arg Gln Glu Leu Asn
        50                  55                  60

Pro Leu Lys Ser Ile Val Glu Lys Ser Ile Leu Leu Thr Glu Gln Ala
65              70                  75                  80

Leu Ala Lys Ala Gly Lys Gly Met His Gly Val Pro Gly Gly Lys
            85                  90                  95

Gln Phe Ile Glu Asn Gly Ser Glu Phe Ala Gln Lys Leu Leu Lys Lys
            100                 105                 110

Phe Ser Leu Leu Lys Pro Trp Ala Gly Leu Val Pro Arg Gly Ser Gly
            115                 120                 125

Val Pro Gly Val Gly Val Pro Gly Val Gly Val Pro Gly Val Gly Val
            130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
            165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
            195                 200                 205

Val Pro Gly Val Gly Val Pro Gly Val Gly Val Pro Gly Val Gly Val
            210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
            245                 250                 255
Val Gly Val Pro Gly Val Gly Val Pro Gly Val Gly Val Pro Gly Val
        260                 265                 270
Gly Val Pro Gly Val Gly Val Pro Gly Val Gly Val Pro Gly Val Gly
    275                 280                 285
Val Pro Gly Val Gly Val Pro Gly Val Gly Val Pro Gly Val Gly Val
290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
            325                 330                 335
Val Gly Val Pro Gly Val Gly Val Pro Gly Val Gly Val Pro Gly Val
        340                 345                 350
Gly Val Pro Gly Val Gly Val Pro Gly Val Gly Val Pro Gly Val Gly
    355                 360                 365
Val Pro Gly Val Gly Val Pro Gly Val Gly Val Pro Gly Val Gly Val
370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
            405                 410                 415
Val Gly Val Pro Gly Val Gly Val Pro Gly Val Gly Val Pro Gly Val
        420                 425                 430
Gly Val Pro Gly Val Gly Val Pro Gly Val Gly Val Pro Gly Val Gly
    435                 440                 445
Val Pro Gly Val Gly Val Pro Gly Val Gly Val Pro Gly Val Gly Val
450                 455                 460
Pro Gly Val Gly Val Pro Gly Val Gly Val Pro Gly Val Gly Val Pro
465                 470                 475                 480
Gly Val Gly Val Pro Gly Val Gly Val Pro Gly Val Gly Val Pro Gly
            485                 490                 495
Val Gly Val Pro Gly Val Gly Val Pro Gly Val Gly Val Pro Gly Val
        500                 505                 510
Gly Val Pro Gly Val Gly Val Pro Gly Val Gly Val Pro Gly Val Gly
    515                 520                 525
Val Pro Gly Val Gly Val Pro Gly Val Gly Val Pro Gly Val Gly Val
530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
            565                 570                 575
Val Gly Val Pro Gly Val Gly Val Pro Gly Val Gly Val Pro Gly Val
        580                 585                 590
Gly Val Pro Gly Val Gly Val Pro Gly Val Gly Val Pro Gly Val Gly
    595                 600                 605
Tyr

<210> SEQ ID NO 15
<211> LENGTH: 609
<212> TYPE: PRT
<213> ORGANISM: Artificial Sequence
<220> FEATURE:
<223> OTHER INFORMATION: LAC-I96

```
<400> SEQUENCE: 15

Met Glu Asp Ala Ser Ser Asp Ser Thr Gly Ala Asp Pro Ala Gln Glu
1               5                   10                  15

Ala Gly Thr Ser Lys Pro Asn Glu Glu Ile Ser Gly Pro Ala Glu Pro
            20                  25                  30

Ala Ser Pro Pro Glu Thr Thr Thr Ala Gln Glu Thr Ser Ala Ala
        35                  40                  45

Ala Val Gln Gly Thr Ala Lys Val Thr Ser Ser Arg Gln Glu Leu Asn
    50                  55                  60

Pro Leu Lys Ser Ile Val Glu Lys Ser Ile Leu Leu Thr Glu Gln Ala
65                  70                  75                  80

Leu Ala Lys Ala Gly Lys Gly Met His Gly Val Pro Gly Gly Lys
                85                  90                  95

Gln Phe Ile Glu Asn Gly Ser Glu Phe Ala Gln Lys Leu Leu Lys Lys
                100                 105                 110

Phe Ser Leu Leu Lys Pro Trp Ala Gly Leu Val Pro Arg Gly Ser Gly
            115                 120                 125

Val Pro Gly Ile Gly Val Pro Gly Ile Gly Val Pro Gly Ile Gly Val
    130                 135                 140

Pro Gly Ile Gly Val Pro Gly Ile Gly Val Pro Gly Ile Gly Val Pro
145                 150                 155                 160

Gly Ile Gly Val Pro Gly Ile Gly Val Pro Gly Ile Gly Val Pro Gly
                165                 170                 175

Ile Gly Val Pro Gly Ile Gly Val Pro Gly Ile Gly Val Pro Gly Ile
            180                 185                 190

Gly Val Pro Gly Ile Gly Val Pro Gly Ile Gly Val Pro Gly Ile Gly
        195                 200                 205

Val Pro Gly Ile Gly Val Pro Gly Ile Gly Val Pro Gly Ile Gly Val
    210                 215                 220

Pro Gly Ile Gly Val Pro Gly Ile Gly Val Pro Gly Ile Gly Val Pro
225                 230                 235                 240

Gly Ile Gly Val Pro Gly Ile Gly Val Pro Gly Ile Gly Val Pro Gly
                245                 250                 255

Ile Gly Val Pro Gly Ile Gly Val Pro Gly Ile Gly Val Pro Gly Ile
            260                 265                 270

Gly Val Pro Gly Ile Gly Val Pro Gly Ile Gly Val Pro Gly Ile Gly
        275                 280                 285

Val Pro Gly Ile Gly Val Pro Gly Ile Gly Val Pro Gly Ile Gly Val
    290                 295                 300

Pro Gly Ile Gly Val Pro Gly Ile Gly Val Pro Gly Ile Gly Val Pro
305                 310                 315                 320

Gly Ile Gly Val Pro Gly Ile Gly Val Pro Gly Ile Gly Val Pro Gly
                325                 330                 335

Ile Gly Val Pro Gly Ile Gly Val Pro Gly Ile Gly Val Pro Gly Ile
            340                 345                 350

Gly Val Pro Gly Ile Gly Val Pro Gly Ile Gly Val Pro Gly Ile Gly
        355                 360                 365

Val Pro Gly Ile Gly Val Pro Gly Ile Gly Val Pro Gly Ile Gly Val
    370                 375                 380

Pro Gly Ile Gly Val Pro Gly Ile Gly Val Pro Gly Ile Gly Val Pro
385                 390                 395                 400

Gly Ile Gly Val Pro Gly Ile Gly Val Pro Gly Ile Gly Val Pro Gly
                405                 410                 415
```

```
Ile Gly Val Pro Gly Ile Gly Val Pro Gly Ile Gly Val Pro Gly Ile
            420                 425                 430
Gly Val Pro Gly Ile Gly Val Pro Gly Ile Gly Val Pro Gly Ile Gly
        435                 440                 445
Val Pro Gly Ile Gly Val Pro Gly Ile Gly Val Pro Gly Ile Gly Val
    450                 455                 460
Pro Gly Ile Gly Val Pro Gly Ile Gly Val Pro Gly Ile Gly Val Pro
465                 470                 475                 480
Gly Ile Gly Val Pro Gly Ile Gly Val Pro Gly Ile Gly Val Pro Gly
                485                 490                 495
Ile Gly Val Pro Gly Ile Gly Val Pro Gly Ile Gly Val Pro Gly Ile
            500                 505                 510
Gly Val Pro Gly Ile Gly Val Pro Gly Ile Gly Val Pro Gly Ile Gly
        515                 520                 525
Val Pro Gly Ile Gly Val Pro Gly Ile Gly Val Pro Gly Ile Gly Val
    530                 535                 540
Pro Gly Ile Gly Val Pro Gly Ile Gly Val Pro Gly Ile Gly Val Pro
545                 550                 555                 560
Gly Ile Gly Val Pro Gly Ile Gly Val Pro Gly Ile Gly Val Pro Gly
                565                 570                 575
Ile Gly Val Pro Gly Ile Gly Val Pro Gly Ile Gly Val Pro Gly Ile
            580                 585                 590
Gly Val Pro Gly Ile Gly Val Pro Gly Ile Gly Val Pro Gly Ile Gly
        595                 600                 605
Tyr

<210> SEQ ID NO 16
<211> LENGTH: 609
<212> TYPE: PRT
<213> ORGANISM: Artificial Sequence
<220> FEATURE:
<223> OTHER INFORMATION: LAC-S96

<400> SEQUENCE: 16

Met Glu Asp Ala Ser Ser Asp Ser Thr Gly Ala Asp Pro Ala Gln Glu
1               5                   10                  15
Ala Gly Thr Ser Lys Pro Asn Glu Glu Ile Ser Gly Pro Ala Glu Pro
            20                  25                  30
Ala Ser Pro Pro Glu Thr Thr Thr Ala Gln Glu Thr Ser Ala Ala
        35                  40                  45
Ala Val Gln Gly Thr Ala Lys Val Thr Ser Ser Arg Gln Glu Leu Asn
    50                  55                  60
Pro Leu Lys Ser Ile Val Glu Lys Ser Ile Leu Leu Thr Glu Gln Ala
65                  70                  75                  80
Leu Ala Lys Ala Gly Lys Gly Met His Gly Val Pro Gly Gly Lys
                85                  90                  95
Gln Phe Ile Glu Asn Gly Ser Glu Phe Ala Gln Lys Leu Leu Lys Lys
            100                 105                 110
Phe Ser Leu Leu Lys Pro Trp Ala Gly Leu Val Pro Arg Gly Ser Gly
        115                 120                 125
Val Pro Gly Ser Gly Val Pro Gly Ser Gly Val Pro Gly Ser Gly Val
    130                 135                 140
Pro Gly Ser Gly Val Pro Gly Ser Gly Val Pro Gly Ser Gly Val Pro
145                 150                 155                 160
```

Gly Ser Gly Val Pro Gly Ser Gly Val Pro Gly Ser Gly Val Pro Gly
            165                 170                 175
Ser Gly Val Pro Gly Ser Gly Val Pro Gly Ser Gly Val Pro Gly Ser
            180                 185                 190
Gly Val Pro Gly Ser Gly Val Pro Gly Ser Gly Val Pro Gly Ser Gly
            195                 200                 205
Val Pro Gly Ser Gly Val Pro Gly Ser Gly Val Pro Gly Ser Gly Val
            210                 215                 220
Pro Gly Ser Gly Val Pro Gly Ser Gly Val Pro Gly Ser Gly Val Pro
225                 230                 235                 240
Gly Ser Gly Val Pro Gly Ser Gly Val Pro Gly Ser Gly Val Pro Gly
            245                 250                 255
Ser Gly Val Pro Gly Ser Gly Val Pro Gly Ser Gly Val Pro Gly Ser
            260                 265                 270
Gly Val Pro Gly Ser Gly Val Pro Gly Ser Gly Val Pro Gly Ser Gly
            275                 280                 285
Val Pro Gly Ser Gly Val Pro Gly Ser Gly Val Pro Gly Ser Gly Val
            290                 295                 300
Pro Gly Ser Gly Val Pro Gly Ser Gly Val Pro Gly Ser Gly Val Pro
305                 310                 315                 320
Gly Ser Gly Val Pro Gly Ser Gly Val Pro Gly Ser Gly Val Pro Gly
            325                 330                 335
Ser Gly Val Pro Gly Ser Gly Val Pro Gly Ser Gly Val Pro Gly Ser
            340                 345                 350
Gly Val Pro Gly Ser Gly Val Pro Gly Ser Gly Val Pro Gly Ser Gly
            355                 360                 365
Val Pro Gly Ser Gly Val Pro Gly Ser Gly Val Pro Gly Ser Gly Val
            370                 375                 380
Pro Gly Ser Gly Val Pro Gly Ser Gly Val Pro Gly Ser Gly Val Pro
385                 390                 395                 400
Gly Ser Gly Val Pro Gly Ser Gly Val Pro Gly Ser Gly Val Pro Gly
            405                 410                 415
Ser Gly Val Pro Gly Ser Gly Val Pro Gly Ser Gly Val Pro Gly Ser
            420                 425                 430
Gly Val Pro Gly Ser Gly Val Pro Gly Ser Gly Val Pro Gly Ser Gly
            435                 440                 445
Val Pro Gly Ser Gly Val Pro Gly Ser Gly Val Pro Gly Ser Gly Val
            450                 455                 460
Pro Gly Ser Gly Val Pro Gly Ser Gly Val Pro Gly Ser Gly Val Pro
465                 470                 475                 480
Gly Ser Gly Val Pro Gly Ser Gly Val Pro Gly Ser Gly Val Pro Gly
            485                 490                 495
Ser Gly Val Pro Gly Ser Gly Val Pro Gly Ser Gly Val Pro Gly Ser
            500                 505                 510
Gly Val Pro Gly Ser Gly Val Pro Gly Ser Gly Val Pro Gly Ser Gly
            515                 520                 525
Val Pro Gly Ser Gly Val Pro Gly Ser Gly Val Pro Gly Ser Gly Val
            530                 535                 540
Pro Gly Ser Gly Val Pro Gly Ser Gly Val Pro Gly Ser Gly Val Pro
545                 550                 555                 560
Gly Ser Gly Val Pro Gly Ser Gly Val Pro Gly Ser Gly Val Pro Gly
            565                 570                 575
Ser Gly Val Pro Gly Ser Gly Val Pro Gly Ser Gly Val Pro Gly Ser

-continued

```
            580                 585                 590
Gly Val Pro Gly Ser Gly Val Pro Gly Ser Gly Val Pro Gly Ser Gly
            595                 600                 605
Tyr

<210> SEQ ID NO 17
<211> LENGTH: 484
<212> TYPE: PRT
<213> ORGANISM: Artificial Sequence
<220> FEATURE:
<223> OTHER INFORMATION: V96

<400> SEQUENCE: 17

Gly Ser Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Val Gly Val Pro Gly Val Gly
            35                  40                  45
Val Pro Gly Val Gly Val Pro Gly Val Gly Val Pro Gly Val Gly Val
        50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
                85                  90                  95
Val Gly Val Pro Gly Val Gly Val Pro Gly Val Gly Val Pro Gly Val
                100                 105                 110
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
        130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                165                 170                 175
Val Gly Val Pro Gly Val Gly Val Pro Gly Val Gly Val Pro Gly Val
                180                 185                 190
Gly Val Pro Gly Val Gly Val Pro Gly Val Gly Val Pro Gly Val Gly
            195                 200                 205
Val Pro Gly Val Gly Val Pro Gly Val Gly Val Pro Gly Val Gly Val
        210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
                260                 265                 270
Gly Val Pro Gly Val Gly Val Pro Gly Val Gly Val Pro Gly Val Gly
            275                 280                 285
Val Pro Gly Val Gly Val Pro Gly Val Gly Val Pro Gly Val Gly Val
        290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
                325                 330                 335
```

```
Val Gly Val Pro Gly Val Gly Val Pro Gly Val Gly Val
            340                 345                 350

Gly Val Pro Gly Val Gly Val Pro Gly Val Gly Val Pro Gly Val Gly
            355                 360                 365

Val Pro Gly Val Gly Val Pro Gly Val Gly Val Pro Gly Val Gly Val
    370                 375                 380

Pro Gly Val Gly Val Pro Gly Val Gly Val Pro Gly Val Gly Val Pro
385                 390                 395                 400

Gly Val Gly Val Pro Gly Val Gly Val Pro Gly Val Gly Val Pro Gly
            405                 410                 415

Val Gly Val Pro Gly Val Gly Val Pro Gly Val Gly Val Pro Gly Val
            420                 425                 430

Gly Val Pro Gly Val Gly Val Pro Gly Val Gly Val Pro Gly Val Gly
            435                 440                 445

Val Pro Gly Val Gly Val Pro Gly Val Gly Val Pro Gly Val Gly Val
    450                 455                 460

Pro Gly Val Gly Val Pro Gly Val Gly Val Pro Gly Val Gly Val Pro
465                 470                 475                 480

Gly Val Gly Tyr

<210> SEQ ID NO 18
<211> LENGTH: 609
<212> TYPE: PRT
<213> ORGANISM: Artificial Sequence
<220> FEATURE:
<223> OTHER INFORMATION: LAC-S48I48

<400> SEQUENCE: 18

Met Glu Asp Ala Ser Ser Asp Ser Thr Gly Ala Asp Pro Ala Gln Glu
1               5                   10                  15

Ala Gly Thr Ser Lys Pro Asn Glu Glu Ile Ser Gly Pro Ala Glu Pro
            20                  25                  30

Ala Ser Pro Pro Glu Thr Thr Thr Ala Gln Glu Thr Ser Ala Ala
        35                  40                  45

Ala Val Gln Gly Thr Ala Lys Val Thr Ser Ser Arg Gln Glu Leu Asn
    50                  55                  60

Pro Leu Lys Ser Ile Val Glu Lys Ser Ile Leu Leu Thr Glu Gln Ala
65                  70                  75                  80

Leu Ala Lys Ala Gly Lys Gly Met His Gly Val Pro Gly Gly Lys
            85                  90                  95

Gln Phe Ile Glu Asn Gly Ser Glu Phe Ala Gln Lys Leu Leu Lys Lys
            100                 105                 110

Phe Ser Leu Leu Lys Pro Trp Ala Gly Leu Val Pro Arg Gly Ser Gly
            115                 120                 125

Val Pro Gly Ser Gly Val Pro Gly Ser Gly Val Pro Gly Ser Gly Val
            130                 135                 140

Pro Gly Ser Gly Val Pro Gly Ser Gly Val Pro Gly Ser Gly Val Pro
145                 150                 155                 160

Gly Ser Gly Val Pro Gly Ser Gly Val Pro Gly Ser Gly Val Pro Gly
            165                 170                 175

Ser Gly Val Pro Gly Ser Gly Val Pro Gly Ser Gly Val Pro Gly Ser
            180                 185                 190

Gly Val Pro Gly Ser Gly Val Pro Gly Ser Gly Val Pro Gly Ser Gly
            195                 200                 205
```

Val Pro Gly Ser Gly Val Pro Gly Ser Gly Val Pro Gly Ser Gly Val
    210                 215                 220

Pro Gly Ser Gly Val Pro Gly Ser Gly Val Pro Gly Ser Gly Val Pro
225                 230                 235                 240

Gly Ser Gly Val Pro Gly Ser Gly Val Pro Gly Ser Gly Val Pro Gly
            245                 250                 255

Ser Gly Val Pro Gly Ser Gly Val Pro Gly Ser Gly Val Pro Gly Ser
        260                 265                 270

Gly Val Pro Gly Ser Gly Val Pro Gly Ser Gly Val Pro Gly Ser Gly
    275                 280                 285

Val Pro Gly Ser Gly Val Pro Gly Ser Gly Val Pro Gly Ser Gly Val
290                 295                 300

Pro Gly Ser Gly Val Pro Gly Ser Gly Val Pro Gly Ser Gly Val Pro
305                 310                 315                 320

Gly Ser Gly Val Pro Gly Ser Gly Val Pro Gly Ser Gly Val Pro Gly
            325                 330                 335

Ser Gly Val Pro Gly Ser Gly Val Pro Gly Ser Gly Val Pro Gly Ser
        340                 345                 350

Gly Val Pro Gly Ser Gly Val Pro Gly Ser Gly Val Pro Gly Ser Gly
    355                 360                 365

Val Pro Gly Ile Gly Val Pro Gly Ile Gly Val Pro Gly Ile Gly Val
370                 375                 380

Pro Gly Ile Gly Val Pro Gly Ile Gly Val Pro Gly Ile Gly Val Pro
385                 390                 395                 400

Gly Ile Gly Val Pro Gly Ile Gly Val Pro Gly Ile Gly Val Pro Gly
            405                 410                 415

Ile Gly Val Pro Gly Ile Gly Val Pro Gly Ile Gly Val Pro Gly Ile
        420                 425                 430

Gly Val Pro Gly Ile Gly Val Pro Gly Ile Gly Val Pro Gly Ile Gly
    435                 440                 445

Val Pro Gly Ile Gly Val Pro Gly Ile Gly Val Pro Gly Ile Gly Val
    450                 455                 460

Pro Gly Ile Gly Val Pro Gly Ile Gly Val Pro Gly Ile Gly Val Pro
465                 470                 475                 480

Gly Ile Gly Val Pro Gly Ile Gly Val Pro Gly Ile Gly Val Pro Gly
            485                 490                 495

Ile Gly Val Pro Gly Ile Gly Val Pro Gly Ile Gly Val Pro Gly Ile
        500                 505                 510

Gly Val Pro Gly Ile Gly Val Pro Gly Ile Gly Val Pro Gly Ile Gly
    515                 520                 525

Val Pro Gly Ile Gly Val Pro Gly Ile Gly Val Pro Gly Ile Gly Val
530                 535                 540

Pro Gly Ile Gly Val Pro Gly Ile Gly Val Pro Gly Ile Gly Val Pro
545                 550                 555                 560

Gly Ile Gly Val Pro Gly Ile Gly Val Pro Gly Ile Gly Val Pro Gly
            565                 570                 575

Ile Gly Val Pro Gly Ile Gly Val Pro Gly Ile Gly Val Pro Gly Ile
        580                 585                 590

Gly Val Pro Gly Ile Gly Val Pro Gly Ile Gly Val Pro Gly Ile Gly
    595                 600                 605

Tyr

<210> SEQ ID NO 19

```
<211> LENGTH: 5
<212> TYPE: PRT
<213> ORGANISM: Artificial Sequence
<220> FEATURE:
<223> OTHER INFORMATION: GENERIC TAG 1
<220> FEATURE:
<221> NAME/KEY: misc_feature
<222> LOCATION: (4)..(4)
<223> OTHER INFORMATION: Xaa can be any naturally occurring amino acid

<400> SEQUENCE: 19

Val Pro Gly Xaa Gly
1               5

<210> SEQ ID NO 20
<211> LENGTH: 6
<212> TYPE: PRT
<213> ORGANISM: Artificial Sequence
<220> FEATURE:
<223> OTHER INFORMATION: GENERIC TAG 2
<220> FEATURE:
<221> NAME/KEY: misc_feature
<222> LOCATION: (4)..(4)
<223> OTHER INFORMATION: Xaa can be any naturally occurring amino acid

<400> SEQUENCE: 20

Val Pro Gly Xaa Gly Gly
1               5

<210> SEQ ID NO 21
<211> LENGTH: 126
<212> TYPE: PRT
<213> ORGANISM: Artificial Sequence
<220> FEATURE:
<223> OTHER INFORMATION: LACRITIN PROTEASE PRODUCT 1

<400> SEQUENCE: 21

Met Gly Glu Asp Ala Ser Ser Asp Ser Thr Gly Ala Asp Pro Ala Gln
1               5                   10                  15

Glu Ala Gly Thr Ser Lys Pro Asn Glu Glu Ile Ser Gly Pro Ala Glu
            20                  25                  30

Pro Ala Ser Pro Pro Glu Thr Thr Thr Thr Ala Gln Glu Thr Ser Ala
        35                  40                  45

Ala Ala Val Gln Gly Thr Ala Lys Val Thr Ser Ser Arg Gln Glu Leu
    50                  55                  60

Asn Pro Leu Lys Ser Ile Val Glu Lys Ser Ile Leu Leu Thr Glu Gln
65                  70                  75                  80

Ala Leu Ala Lys Ala Gly Lys Gly Met His Gly Gly Val Pro Gly Gly
                85                  90                  95

Lys Gln Phe Ile Glu Asn Gly Ser Glu Phe Ala Gln Lys Leu Leu Lys
            100                 105                 110

Lys Phe Ser Leu Leu Lys Pro Trp Ala Gly Leu Val Pro Arg
        115                 120                 125

<210> SEQ ID NO 22
<211> LENGTH: 118
<212> TYPE: PRT
<213> ORGANISM: Artificial Sequence
<220> FEATURE:
<223> OTHER INFORMATION: LACRITIN PROTEASE PRODUCT 2

<400> SEQUENCE: 22

Met Gly Glu Asp Ala Ser Ser Asp Ser Thr Gly Ala Asp Pro Ala Gln
1               5                   10                  15
```

```
Glu Ala Gly Thr Ser Lys Pro Asn Glu Ile Ser Gly Pro Ala Glu
                20                  25                  30

Pro Ala Ser Pro Pro Glu Thr Thr Thr Thr Ala Gln Glu Thr Ser Ala
        35                  40                  45

Ala Ala Val Gln Gly Thr Ala Lys Val Thr Ser Ser Arg Gln Glu Leu
    50                  55                  60

Asn Pro Leu Lys Ser Ile Val Glu Lys Ser Ile Leu Leu Thr Glu Gln
 65                 70                  75                  80

Ala Leu Ala Lys Ala Gly Lys Gly Met His Gly Gly Val Pro Gly Gly
                85                  90                  95

Lys Gln Phe Ile Glu Asn Gly Ser Glu Phe Ala Gln Lys Leu Leu Lys
                100                 105                 110

Lys Phe Ser Leu Leu Lys
            115

<210> SEQ ID NO 23
<211> LENGTH: 119
<212> TYPE: PRT
<213> ORGANISM: Artificial Sequence
<220> FEATURE:
<223> OTHER INFORMATION: LACRITIN PROTEASE PRODUCT 3

<400> SEQUENCE: 23

Met Gly Glu Asp Ala Ser Ser Asp Ser Thr Gly Ala Asp Pro Ala Gln
 1               5                  10                  15

Glu Ala Gly Thr Ser Lys Pro Asn Glu Ile Ser Gly Pro Ala Glu
                20                  25                  30

Pro Ala Ser Pro Pro Glu Thr Thr Thr Thr Ala Gln Glu Thr Ser Ala
        35                  40                  45

Ala Ala Val Gln Gly Thr Ala Lys Val Thr Ser Ser Arg Gln Glu Leu
    50                  55                  60

Asn Pro Leu Lys Ser Ile Val Glu Lys Ser Ile Leu Leu Thr Glu Gln
 65                 70                  75                  80

Ala Leu Ala Lys Ala Gly Lys Gly Met His Gly Gly Val Pro Gly Gly
                85                  90                  95

Lys Gln Phe Ile Glu Asn Gly Ser Glu Phe Ala Gln Lys Leu Leu Lys
                100                 105                 110

Lys Phe Ser Leu Leu Lys Lys
            115

<210> SEQ ID NO 24
<211> LENGTH: 62
<212> TYPE: PRT
<213> ORGANISM: Artificial Sequence
<220> FEATURE:
<223> OTHER INFORMATION: LACRITIN PROTEASE PRODUCT 4

<400> SEQUENCE: 24

Pro Asn Glu Glu Ile Ser Gly Pro Ala Glu Pro Ala Ser Pro Pro Glu
 1               5                  10                  15

Thr Thr Thr Thr Ala Gln Glu Thr Ser Ala Ala Ala Val Gln Gly Thr
                20                  25                  30

Ala Lys Val Thr Ser Ser Arg Gln Glu Leu Asn Pro Leu Lys Ser Ile
            35                  40                  45

Val Glu Lys Ser Ile Leu Leu Thr Glu Gln Ala Leu Ala Lys
    50                  55                  60
```

CONTROLLED RELEASE OF OCULAR BIOPHARMACEUTICALS USING BIORESPONSIVE PROTEIN POLYMERS

CROSS REFERENCE TO RELATED APPLICATIONS

This application includes a claim of priority under 35 U.S.C. §119(e) to U.S. Patent Application No. 61/511,928, filed Jul. 26, 2011.

GOVERNMENT RIGHTS

This invention was made with government support under Contract No. R21EB012281-01 awarded by the National Institutes of Health. The government has certain rights in the invention.

FIELD OF INVENTION

This invention relates to the use of protein polymers to improve drug delivery to various organs, particularly the eye, and other related uses.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Affecting over 3.2 million Americans, dry eye syndrome is a common disorder of the tear film characterized by decreased tear production. This disease is prevalent among the elderly and is particularly common in postmenopausal women. Typically, dry eye is treated using conventional drops containing small molecule drugs, although recombinant tear protein rescue for dry eye syndrome has become a possibility with the discovery of a novel human tear glycoprotein, lacritin. Lacritin is capable of promoting basal tear peroxidase secretion by rat lacrimal acinar cells in vitro, basal tear secretion by rabbit in vivo and possibly triggers downstream signaling pathway through tyrosine phosphorylation and calcium release. However, this option has found limited practical application as tears wash drugs away from the eye within minutes, and less than 2% of the medication is absorbed. As tears rapidly wash away both small and large molecule drugs, this has prevented the development of numerous protein-based drugs. By contrast, protein drugs administered to other sites in the body have continued to be developed into effective therapies. Thus, there is a clear unmet need to develop effective delivery strategies that for administration and retention of biopharmaceuticals in a target organ, such as the surface of the eye.

Accordingly, the inventive compositions and methods disclosed herein establish new and improved techniques for improving drug delivery to organs that are presently limited by biochemical and biomechanical environments due to pH, temperature, hydrodynamic flow, mechanical/structure features, among others. To overcome these obstacles, the inventors have developed temperature sensitive protein polymers and fused these polymers directly to a biopharmaceutical with enhanced therapeutic activity at the eye surface. This strategy allows for retention of drugs in the eye for much longer periods of time, on the order of days to weeks, thereby improving drug efficacy, while reducing cost and eliminating the need for repeated drug application.

SUMMARY OF THE INVENTION

The present invention provides, in one embodiment, an isolated fusion protein including a bioresponse protein polymer, and a therapeutic protein conjugated to the bioresponse protein polymer. In another embodiment, the bioresponse protein polymer is an elastin-like polypeptide (ELP). In another embodiment, the ELP includes amino acid motif (Val-Pro-Gly-$X_{aa}$-Gly)$_n$ (i.e., n number of [SEQ ID NO. 19]), where n includes 10 to 300 units and $X_{aa}$ is a natural or synthetic amino acid. In another embodiment, n is 96 and $X_{aa}$ is serine, valine, or isoleucine. In another embodiment, therapeutic protein is lacritin, a functional equivalent or active fragment thereof. In another embodiment, lacritin, functional equivalent or active fragment thereof includes human lacritin. In another embodiment, the lacritin, functional equivalent or active fragment thereof includes amino acid sequence: SEQ ID NO: 3, SEQ ID NO: 4, SEQ ID NO: 5, SEQ ID NO: 6, SEQ ID NO: 7, or SEQ ID NO: 8. In another embodiment, the bioresponse protein polymer and therapeutic protein are conjugated via a linker peptide. In another embodiment, the linker peptide includes amino acid sequence: SEQ ID NO: 9. In another embodiment, the bioresponse protein polymer is ELP, the therapeutic protein is lacritin, and the ELP is conjugated to the lacritin via a linker peptide. In another embodiment, the fusion protein includes an ELP including amino acid motif (Val-Pro-Gly-$X_{aa}$-Gly)$_n$ (i.e., n number of [SEQ ID NO. 19]), n is 96 and $X_{aa}$ is valine, conjugated to a lacritin, functional equivalent or active fragment thereof including amino acid sequence: SEQ ID NO: 3, SEQ ID NO: 4, SEQ ID NO: 5, SEQ ID NO: 6, SEQ ID NO: 7, or SEQ ID NO: 8, via a linker peptide including SEQ ID NO:9.

Another aspect of the present invention provides, in one embodiment, an isolated nucleotide encoding a fusion protein including a bioresponse protein polymer, and a therapeutic protein conjugated to the bioresponse protein polymer. In another embodiment, the bioresponse protein polymer includes an elastin-like polypeptide (ELP). In another embodiment, the ELP includes amino acid motif (Val-Pro-Gly-$X_{aa}$-Gly)$_n$ (i.e., n number of [SEQ ID NO. 19]), where n includes 10 to 300 repeat units and $X_{aa}$ is a natural or synthetic amino acid. In another embodiment, the therapeutic protein includes lacritin, a functional equivalent or active fragment thereof. In another embodiment, the isolated nucleotide of is constructed using recursive directional ligation. In another embodiment, the isolated nucleotide encodes for a fusion protein including an ELP including amino acid motif (Val-Pro-Gly-$X_{aa}$-Gly)$_n$ (i.e., n number of [SEQ ID NO. 19]), n is 96 and $X_{aa}$ is valine, conjugated to a lacritin, functional equivalent or active fragment thereof including amino acid sequence: SEQ ID NO: 3, SEQ ID NO: 4, SEQ ID NO: 5, SEQ ID NO: 6, SEQ ID NO: 7, or SEQ ID NO: 8, via a linker peptide including SEQ ID NO:9.

Another aspect of the present invention provides, in one embodiment, a method of treating a disease and/or condition in a human subject, include providing a quantity of a composition, wherein the composition includes a fusion protein, the fusion protein including a bioresponse protein polymer and a therapeutic protein conjugated to the bioresponse protein polymer; and treating a human subject by administering a therapeutically effective dosage of the composition to the subject, thereby treating the subject. In another embodiment, the human subject is in need of treatment for an eye disease and/or condition selected from the group consisting of: acanthamoeba keratitis, allergies, amblyopia, Bell's palsy, blepharitis, cataracts, chalazion, color blindness, corneal ulcer, detached retina, dry eye syndrome, keratoconjunctivitis sicca, eye occlusions, eye twitching, macular hole, nystagmus, ocular migraine, ocular rosacea, optic neuritis, optic neuropathy, photophobia, pinguecula, pterygium, ptosis, Sjogren's syndrome, strabismus, stye, subconjunctival hemorrhage, uveitis, CMV retinitis, conjunctivitis, diabetic retinopathy, eye herpes, glaucoma, karatoconus, macular degeneration, macular dystrophy, ocular hypertension, retinitis pigmentosa, and/or Stargardt's disease. In another embodiment, the bioresponse protein polymer includes an elastin-like polypeptide (ELP), the therapeutic protein includes lacritin, and the ELP is conjugated to the lacritin via a linker peptide.

Another aspect of the present invention provides, in one embodiment, a pharmaceutical composition including a bioresponse protein polymer, a therapeutic protein conjugated to the bioresponse protein polymer, and a pharmaceutically acceptable carrier. In another embodiment, the bioresponse protein polymer includes an elastin-like polypeptide (ELP), the therapeutic protein includes lacritin, and the ELP is conjugated to the lacritin via a linker peptide.

Another aspect of the present invention provides, in one embodiment, a a method of using an ELP in a purification process, including: a) providing a sample including a ELP construct, b) inducing phase transition in the sample by adding 0 to 20 M NaCl and heating to temperatures up to about 10, 20, 30, 35, 37, 40, or 45° C., b) centrifuging the sample at 5,000, 6,000, 7,000, 8,000, 9,000 or 10,000 g, c) discarding the supernatant, and d) cooling remaining pellet to about, 1, 2, 3, 4, 5, or 6-10° C.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 ELP protein polymers. (A): Cartoon showing Lac-ELP fusion protein stimulates primary rabbit lacrimal gland acinar cells (LGACs) secretion. (B): Elastin-like polypeptides (ELPs) phase transition. (C): Cartoon showing drug delivery to the eye via topical administration or lacrimal gland injection.

FIG. 2. Examples of Lac-ELPs. (A): Cartoon showing structure of a typical Lac-ELP fusion protein. Lacritin and ELP tag are at the N and C terminus of the fusion construct accordingly. A thrombin recognition site (GLVPR|GS) is designed between the two moieties for releasing free lacritin. Four types of ELP tags are chosen: I96 [SEQ ID NO: 11], V96 [SEQ ID NO: 17], S96 [SEQ ID NO: 12] and S48 I48 [SEQ ID NO: 13]. (B): Sequence, M.W. and Phase Transition Temperature ($T_t$) characterization of Lac-ELP library. At $T<T_t$, ELPs exist as soluble monomers; at $T>T_t$, monoblock S96 stay soluble as 2-3 nm monomers; more hydrophonbic I96, V96 self-assemble into micron-sized coacervates (>1 µm). Diblock ELPs (S48I48) undergo two transitions: one smooth transition from 2-3 nm monomer to 20 nm micelles at CMT (26.6° C.) and one sharp bulk phase transition at 75° C. Lac-ELPs exhibit different phase transition behavior from their parent ELPs based on particular guest residues. Both Lac-I96 and Lac-V96 exhibited 5° C. decrease of $T_t$ compared to I96 and V96. Lac-S96 completely abolished the phase transition behavior of S96. In contrast to an obvious 2-stage phase transition of S48I48, Lac-S48I48 only shows one sharp phase transition at 18.7° C. *m/z (Expected M.W.) is calculated by DNAStar Lasergene Editseq; [M+H]+(Observed M.W.) is measured by MALDI-TOF; *$T_t$ is characterized at 25 µM in PBS.

FIG. 3. Construction of bacterial expression vector encoding for a lacritin ELP fusion protein. (A): A gene encoding the lacritin between the NdeI and BamHI sites was ligated into a pET25B(+) vector. A technique used by our group called Recursive Directional Ligation was used to create ELP genes that can be extracted by cleavage at a BseRI and the BamHI restriction site. Fusion of the appropriate digested vectors, yields a bacterial expression plasmid that encodes for an in frame fusion protein consisting of an amino terminal lacritin and a carboxy terminal ELP. The two domains are linked by a thrombin cleavage recognition site to enable proteolytic cleavage and purification of the free lacritin. (B): Size exclusion chromatograph of Lac-V96 purification.

FIG. 4. Purity of a lacritin-ELP fusion protein and mass spectrometry analysis. (A): SDS PAGE of copper chloride stained purified lacritin-ELP fusion protein, Lac-V96. Also included are purified ELP alone, V96, and the purified lacritin protein (Lac). (B): Matrix assisted laser desorption ion time of flight (MALDI TOF) was used to confirm the exact masses of the ELP and Lac-V96 fusion proteins. Results of this study are indicated in Table 3; however, these results demonstrate that the correct protein has been expressed and purified using our methods. Lac-ELP fusion gene was biosynthesized using pET25b(+) vector. After expression in BLR(DE3) cells, ELPs and Lac-ELP fusion proteins were purified using Inverse phase transition cycling (ITC) and size exclusion chromatography. Free lacritin was released by thrombin cleavage.

FIG. 5. Further characterization of purity of a Lacririn-ELP fusion protein and mass spectrometry analysis. (A): Another SDS PAGE of copper chloride stained purified lacritin-ELP fusion protein. Lanes from L to R are 1.7: Marker, 2: Lac-V96 After ITC purification, 3: Lac-V96 After size exclusion column purification, 4: V96 After ITC purification, 5: Lac After thrombin cleavage Before hot spin, 6: Lac After thrombin cleavage After hot spin. (B): Another MALDI TOF confirming the exact masses of the ELP and Lac-V96 fusion proteins, demonstrating correct expression of the protein purified using our methods.

FIG. 6. Phase diagrams for lacritin ELP fusion proteins. The fusion protein between lacritin and the ELP V96 displays ELP phase transition behavior. (A): $T_t$ characterization of V96. (B): $T_t$ characterization of Lac-V96. (C): Concentration dependent $T_t$ of V96 and Lac-V96. (D): Above the line depicted for Lac-V96, the fusion protein undergoes phase separation, around 30° C. This fusion construct would therefore be soluble at room temperature and undergo phase separation at the temperature of the ocular surface, which is >32° C. The fusion of lacritin has a detectable, but minimal effect on the transition temperature compared to unmodified ELP.

FIG. 11. Lac-V96 and Lac stimulate LGAC secretion. (A): Time dependent LGAC secretion, bhex level is normalized to total protein secreted using BCA assay, N=3. (B): Concentration dependent LGAC secretion, Values are means+SD of LGAC cell response to each treatment expressed as (Bhex-Treatment−BhexCCh−)/(BhexCCh+−BhexCCh−)*100%. CCh− group response is defined as 0% and CCh+ group response is defined as 100%; N=3. * P<0.05,P<0.01, * P<0.001.

FIG. 13. Lac-ELP and Lac stimulate Syn-GFP secretion. In vitro activity of purified proteins was measured by β-hexosaminidase assay and syncollin-GFP secretion assay using primary rabbit lacrimal gland acinar cells (LGACs). Previous studies have shown that both 13-hexosaminidase and syncollin-GFP can be secreted from rabbit lacrimal gland acinar cells in primary culture on stimulation with secretagogs. (A): schematic outline of LGAC, N: nucleus, L: lumenal regions, SVs: secretory vesicles. (B): 50 µM CCh+, Lac-V96, Lac or V96 was added into Ad-Syn-GFP (green) and LifeAct-RFP (red) double transduced LGACs. Time-lapse pictures were taken using Zeiss LSM 510 Meta NLO (Thornwood, N.Y.) confocal imaging system. Scale bar: 5 µm, *:Lumenal regions, arrows: morphology change in LGAC lumen and Syncollin-GFP secretory vesicles.

DETAILED DESCRIPTION OF THE INVENTION

Figure 7:
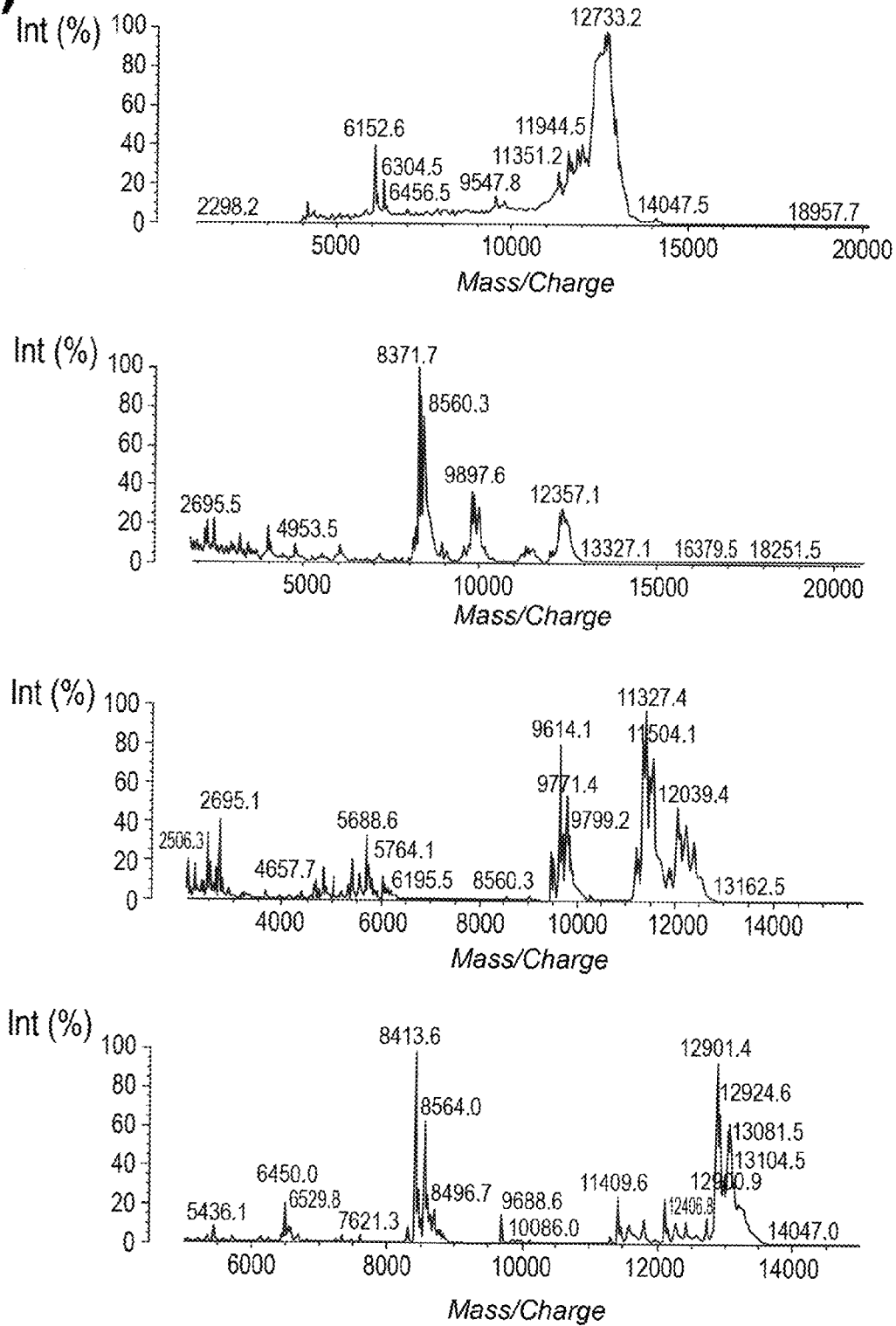
FIG. 7. Lacritin undergoes degradation at 37° C. (A): Time dependent degradation characterization of Lac, fit into one-phase decay curve. (B): Amino acid sequence of Lac, red: K residues. (C): MALDI-TOF analysis of purified lacritin and degraded lacritin, K is expected cutting site. For determination of the degradation half-life of purified Lac-ELPs and lacritin, the purified proteins (20 µg) were incubated in PBS or rabbit tear at 37° C. for 72 h. At each time point, an equal volume of 4×SDS-PAGE loading buffer (2% SDS, 0.01% bromophenol blue, and 63 mM Tris-HCl, pH 6.8, with or without 5% β-mercaptoethanol) was added. The samples were boiled for 5 min at 95° C., and then loaded onto pre-casted 4-20% Tris-HCl polyacrylamide gels (Lonza). β-mercaptoethanol was included in the SDS-PAGE sample buffer to disrupt the possible intrachain and interchain disulfide bonds in protein. The ability of the exogenous protease inhibitors to inactivate degradation was also evaluated. Peptide sequence analysis of degradation was performed using MALDI-TOF. Cleavage products were assigned by MALDI-TOF mass by comparison of measured with predicted mass to charge ratios (m/z) with +1 charge ionization ([M+H]+).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russell, Molecular Cloning: A Laboratory Manual 3rd ed., Cold Spring Harbor Laboratory Press (Cold Spring Harbor, N.Y. 2001), *Remington's Pharmaceutical Sciences*, by E. W. Martin, Mack Publishing Co., Easton, Pa., 15th Edition (1975), describes compositions and formulations suitable for pharmaceutical delivery of the inventive compositions described herein provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i e, inhibition or suppression) of a response or the two in combination or apart.

"Pharmaceutically acceptable carriers" as used herein refer to conventional pharmaceutically acceptable carriers useful in this invention.

"Promote" and/or "promoting" as used herein refer to an augmentation in a particular behavior of a cell or organism.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

The lacrimal gland-cornea axis plays a critical role in maintaining ocular health. While avascular cornea serves as both protective barrier and main refractive element of the visual system, lacrimal gland is the major organ secreting key proteins and electrolytes into the tear film that overspreads the cornea and conjunctiva. Dry eye syndrome is a multifactorial disease of the tears and ocular surface causing visual disturbance and tear film instability. Accordingly to report, severe dry eye disease (DED) affects approximately 5 million Americans above 50 years and its global prevalence ranges from 5% to 35%. Great strides have been made to treat dry eye syndrome and DED through lubricating ocular surface with artificial tears, conserving the secreted tears using tear plugs and eye-shields, or targeting the associated ocular surface inflammation such as Cyclosporin eye-drops. Nevertheless, there still remains a continued demand for efficient, sustained and targeted novel dry eye syndrome and DED therapy.

Ocular drug delivery remains challenging due to the unique ocular anatomy and physiology. Blinking, tear film, and various layers of corneal cells all lead to reduced bioavailability for topical ocular administration. Conventional eye drops are washed away from the eye within minutes after ocular administration, and less than 2% of the medication is absorbed. Due to rapid clearance, ocular drug formulations must be given frequently, every 2 to 8 hours. Further, effective dry eye therapy requires economic process of manufacture, long-term drug stability inside appropriate vehicle and non-invasive prolonged controlled release of the drug to target site. A promising development of safe and effective drug delivery systems is biocompatible polymers, which offer the versatility to remodel drug delivery vesicle structure and further tailor drug release kinetics. Recently, macromolecular self-assemble nanoparticles are emerging as attractive candidates for therapeutic applications.

Elastin-like-polypeptides (ELPs) are one type of such biomaterials. These proteins are members of a larger class of bioresponsive protein polymers that are macromolecules responsive to small environmental changes, for instance temperature or pH. Inspired from human tropoelastin, ELPs have unique properties that promote phase separation, recombinant expression, protein purification, and self-assembly of nanostructures. The polypeptides are biodegradable, biocompatible polymers with temperature-sensitive phase behavior. ELPs are soluble in aqueous solutions below their transition temperature and collapse and aggregate under hydrophobic forces above their critical transition temperature. Importantly, this type of phase transition can be exploited for the development of fusion proteins that are highly soluble at room temperature, but undergo reversible assembly of micron size particles on the ocular surface. These dynamic chemical characteristics can be captured in fusion proteins containing therapeutically effective compounds, thereby allowing retention of biopharmaceuticals in the eye longer than conventional application techniques.

One therapeutically effective compound for use in treating dry eye syndrome is lacritin. lacritin is a 138 amino acid, 12.3 kDa glycoprotein (Uniparc ID NO. Q9GZZ8) secreted in human tears. One of the 4-5% proteins that are downregulated in dry eye syndromes, lacritin is a highly glycosylated tear protein showing prosecretory and mitogenetic activity for corneal epithelial cells. Detected by 2-D PAGE, nano-LC-MS/MS and SELDI studies, lacritin shows a common down-regulation in blepharitis vs normal tears. In vivo studies of lacritin on New Zealand white rabbits shows that eyes treated three times a day for two weeks display a steady rise in tearing that is sustained for at least one week after the last treatment and is well tolerated when topically applied in rabbits. Current ongoing and future research is being carried out to formulate lacritin as a topical eye drop as an effective treatment for dry eye syndrome. However, these rabbit studies have demonstrated that significant effects with lacritin require application of the protein to the ocular surface at least three times a day via eye drops.

The inventors have exploited the features of ELPs in creating a fusion protein containing lacritin, to effectively stimulate ocular surface healing and tear production. By fusing a small library of various ELPs to lacritin, the inventors characterized the phase transition temperatures for the resulting lacritin-ELP constructs and demonstrated that the lacritin contained therein is capable of actively stimulating the tear secretion of primary lacrimal gland acinar cells from rabbits. The most commonly used ELPs consist of pentapeptide repeats of $(VPGX_{aa}G)_n$ (i.e., n number of [SEQ ID NO. 19]), where $X_{aa}$, the guest residue, is any amino acid and n represents the number of repeats in the ELP. ELPs exhibit the unique property of inverse temperature phase transition; they are soluble in aqueous solution below their inverse transition temperature (Tt) and undergo an aqueous demixing above their Tt, resulting in the formation of an insoluble, polymer-rich 'coacervate' phase. This novel application of ELPs exploits their characteristic phase behavior to slow clearance of biologically active proteins from the eye, while also providing a versatile liquid-solid medium scaffold as support for retaining these compounds in the eye.

Described herein are various aspects of the present invention. In one embodiment, the present invention provides an isolated fusion protein including a bioresponse protein polymer conjugated to a therapeutic protein. In another embodiment, the isolated fusion protein contains a bioresponse protein polymer that is an elastin-like polypeptide (ELP). In another embodiment, the ELP includes the motif (Val-Pro-Gly-$X_{aa}$-Gly)$_n$ (i.e., n number of [SEQ ID NO. 19]), where n is between 10 and 300 repeat units and $X_{aa}$ is a natural or synthetic amino acid. In another embodiment, the ELP includes the motif (Val-Pro-Gly-$X_{aa}$-Gly)$_n$ (i.e., n number of [SEQ ID NO. 19]), where n is between 10-50, 50-100, 100-150, 150-200, 200-250, 250-300 and/or 300-400 repeat units and $X_{aa}$ is a natural or synthetic amino acid. In other embodiments, $X_{aa}$ is serine, isoleucience, or valine. In one embodiment, n is 96 and $X_{aa}$ is valine.

In another embodiment, the therapeutic protein is lacritin, a functional equivalent or active fragment thereof. In another embodiment, the lacritin, functional equivalent or active fragment thereof is human lacritin. In another embodiment, the lacritin, functional equivalent or active fragment thereof is an amino acid sequence with 70, 75, 80, 85, 90, 95, 99, or 100% similarity to SEQ ID NO: 3. In another embodiment, the lacritin, functional equivalent or active fragment thereof is amino acid sequence SEQ ID NO: 4, SEQ ID NO: 5, SEQ ID NO: 6, SEQ ID NO: 7, or SEQ ID NO: 8. In another embodiment, the bioresponse protein polymer and therapeutic protein are conjugated via a linker peptide. In another embodiment, the linker peptide is the amino acid sequence: SEQ ID NO: 9. In another embodiment, the bioresponse protein polymer is ELP, the therapeutic protein is lacritin, and the ELP is conjugated to the lacritin via a linker peptide. In another embodiment, the isolated fusion protein includes the amino acid sequence: SEQ ID NO: 4, SEQ ID NO: 5, SEQ ID NO: 6, SEQ ID NO: 7, or SEQ ID NO: 8, conjugated to amino acid motif $[VPGX_{aa}G]_n$ (i.e., n number of [SEQ ID NO. 19]), wherein n is 96 and $X_{aa}$ is valine. In other embodiments, the therapeutic protein is Restasis (cyclosporin), α-Crystallin, Ocriplasmin, Ranibizumab, aflibercept, iSONEP, or Volociximab.

In other embodiments, ELPs are composed of simple pentapeptide repeat $(VPGX_{aa}G)$. (i.e., n number of [SEQ ID NO. 19]), where the 'guest residue' $X_{aa}$ can be any amino acid and n controls the peptide length. In other embodiments, ELPs possess inverse temperature phase transition behavior, are soluble in aqueous solutions below their transition temperature (Tt), and/or self-assemble into various-sized particles above Tt. In other embodiments, Tt can be precisely modulated by adjusting the length of the pentapetides repeats and the hydrophobicity of the guest residue. In certain embodiments, Tt is calculated according to the following equation:

$$T_t = m\ \mathrm{Log}_{10}[C_{ELP}] + b$$

wherein $C_{ELP}$ (μM) is the ELP concentration, m is the slope (° C. per $\mathrm{Log}_{10}$[μM]), and b (° C.) is the transition temperature at 1 μM. In other embodiments, the ELPs include at least two monomeric amino acid motifs with different guest residues, $(VPGX_{aa}1G)_{n1}(VPGX_{aa}2G)_{n2}$ (i.e., n1 number of [SEQ ID NO. 19] and n2 number of [SEQ ID NO. 20]), where n1 or n2 are each between 10 and 300 repeat units and $X_{aa}$ is a natural or synthetic amino acid. In another embodiment, the ELP includes the motif (Val-Pro-Gly-$X_{aa}$-Gly)$_n$ (i.e., n number of [SEQ ID NO. 19]), where n1 or n2 are each between 10-50, 50-100, 100-150, 150-200, 200-250, 250-300 and/or 300-400 repeat units and $X_{aa}$ is a natural or synthetic amino acid. In other embodiments, $X_{aa}$ is serine, isoleucience, or valine. In one embodiment, n is 48 and $X_{aa}$ is valine.

In another aspect of the present invention, described herein is an isolated nucleotide encoding a fusion protein that includes a bioresponse protein polymer conjugated to a therapeutic protein. In another embodiment, the bioresponse protein polymer is a member of the group of elastins, resilins, collagens, slik- and/or elastin-like polypeptides. In another embodiment, the bioresponse protein polymer is an elastin-like polypeptide (ELP). In another embodiment, the ELP includes the motif $(VPGX_{aa}G)_n$ (i.e., n number of [SEQ ID NO. 19]), where n is between 10 and 300 repeat units and $X_{aa}$ is a natural or synthetic amino acid. In another embodiment, the ELP includes the motif (Val-Pro-Gly-$X_{aa}$-Gly)$_n$ (i.e., n number of [SEQ ID NO. 19]), where n is between 10-50, 50-100, 100-150, 150-200, 200-250, 250-300 and/or 300-400 repeat units and $X_{aa}$ is a natural or synthetic amino acid. In other embodiments, $X_{aa}$ is serine, isoleucience, or valine. In one embodiment, n is 96 and $X_{aa}$ is valine. In another embodiment, the therapeutic protein is lacritin, a functional equivalent or active fragment thereof. In another embodiment, the lacritin, functional equivalent or active fragment thereof is human lacritin In another embodiment, the lacritin, functional equivalent or active fragment thereof is an amino acid sequence with 70, 75, 80, 85, 90, 95, 99, or 100% similarity to SEQ ID NO: 3. In another embodiment, the lacritin, functional equivalent or active fragment thereof is amino acid sequence SEQ ID NO: 4, SEQ ID NO: 5, SEQ ID NO: 6, SEQ ID NO: 7, or SEQ ID NO: 8. In another embodiment, the isolated nucleotide encoding a fusion protein includes polynucleotide sequence SEQ ID NO: 1 or SEQ ID NO:2. In another embodiment, the bioresponse protein polymer is ELP, the therapeutic protein is lacritin, and the ELP is conjugated to the lacritin via a linker peptide. In another embodiment, the linker peptide is the amino acid sequence: SEQ ID NO: 9. In another embodiment, the bioresponse protein polymer and therapeutic protein are conjugated via a linker peptide. In another embodiment, the bioresponse protein polymer is ELP, the therapeutic protein is lacritin, and the ELP is conjugated to the lacritin via a linker peptide. In another embodiment, the isolated fusion protein includes the amino acid sequence: SEQ ID NO: 4, SEQ ID NO: 5, SEQ ID NO: 6, SEQ ID NO: 7, or SEQ ID NO: 8, conjugated to amino acid motif $[VPGX_{aa}G]_n$ (i.e., n number of [SEQ ID NO. 19]), wherein n is 96 and $X_{aa}$ is valine. n other embodiments, the therapeutic protein is Restasis (cyclosporin), α-Crystallin, Ocriplasmin, Ranibizumab, aflibercept, iSONEP, or Volociximab. In another embodiment, the isolated nucleotide is constructed using recursive directional ligation.

In other embodiments, the ELPs are fusion proteins including Lac-ELP fusion proteins. In other embodiments, the Lac-ELP fusion proteins are Lac-I96, Lac-V96, Lac-S96, and/or Lac-S48I48. In other embodiments, the Lac-ELPs are purified by inverse phase transition cycling (ITC), which can further be purified using size exclusion chromatography polishing to remove ELP tag. In another embodiment, free lacritin can be released from purified lacritin-ELP via thrombin cleavage. In other embodiments, Lac-ELPs pre-assemble into 10-60 nm nanoparticles. Above Tt, Lac-I96 and Lac-V96 form micron-sized coacervate while Lac-S48I48 assembles into 100-180 nm micelles. In other embodiments, ELPs are also capable of self-assembling into stable micelles around physiological temperature, such as 37° C. In other embodiments, ELPs organized as stable micelles are used as a drug delivery vehicle, which may further modulate biodistribution and pharmacokinetics of the protein in vivo. In other embodiments, ELPs are applied as a drug delivery vehicle for a therapeutic such as Restasis (cyclosporin), α-Crystallin, Ocriplasmin, Ranibizumab, aflibercept, iSONEP, Volociximab, Sirolimus (rapamycin), Pazopanib, Vatalanib, AL39324, ATG-3, JSM6427, Fasudil, ATS907, AR-12286, K-115, and/or Carbachol.

In another aspect of the present invention, described herein are ELPs that can be used as a purification tag. In one embodiment, the present invention includes a method of using an ELP in a purification process, including: a) providing a sample including a ELP construct, b) inducing phase transition in the sample by adding 0 to 20 M NaCl and heating to temperatures up to about 10, 20, 30, 35, 37, 40, or 45° C., b) centrifuging the sample at 5,000, 6,000, 7,000, 8,000, 9,000 or 10,000 g, c) discarding the supernatant, and d) cooling remaining pellet to about, 1, 2, 3, 4, 5, or 6-10° C. In one embodiment, the sample is further agitated into a solution. In one embodiment, repeated cycles of hot and cold centrifugation are further applied, including 1, 2, 3, 4, 5, 6, 7, 8, 9 or 10 repetitions. In another aspect of the present invention, ELPs that can be used as a purification tag for lacritin, thioredoxin (Trx), chloramphenicol acetyltransferase (CAT), calmodulin (CaM), green fluorescent protein (GFP), and/or Knob.

In another aspect of the present invention, described herein is a method of treating a disease and/or condition in a human subject, which includes providing a quantity of a composition, wherein the composition includes a fusion protein, the fusion protein including a bioresponse protein polymer conjugated to a therapeutic protein; and treating a human subject by administering a therapeutically effective dosage of the composition to the subject, thereby treating the subject. In another embodiment, the human subject is afflicted with a disease and/or condition affecting the organs of the circulatory system, digestive system, endocrine system, integumentary system, lymphatic system, immune system, musculoskeletal system, nervous system, reproductive system, respiratory system, and/or urinary system. Examples include the skin, stomach, intestines, pancreas, liver, and/or brain. In another embodiment, the human subject is in need of treatment for an eye disease and/or condition selected from the group consisting of: acanthamoeba keratitis, allergies, amblyopia, Bell's palsy, blepharitis, cataracts, chalazion, color blindness, corneal ulcer, detached retina, dry eye syndrome, keratoconjunctivitis sicca, eye occlusions, eye twitching, macular hole, nystagmus, ocular migraine, ocular rosacea, optic neuritis, optic neuropathy, photophobia, pinguecula and pterygium, ptosis, Sjogren's syndrome, strabismus, stye, subconjunctival hemorrhage, uveitis, CMV retinitis, conjunctivitis, diabetic retinopathy, eye herpes, glaucoma, karatoconus, macular degeneration, macular dystrophy, ocular hypertension, retinitis pigmentosa, and/or Stargardt's disease. In other embodiments, the drug delivery vehicle is used in combination with a contact lens. In another embodiment, the bioresponse protein polymer is ELP, the therapeutic protein is lacritin, and the ELP is conjugated to the lacritin via a linker peptide.

In another aspect of the present invention, described herein is a pharmaceutical composition, which includes a bioresponse protein polymer conjugated to a therapeutically effective protein and a pharmaceutically acceptable carrier. In another embodiment, bioresponse protein polymer is ELP, the therapeutic protein is lacritin, and the ELP is conjugated to the lacritin via a linker peptide.

EXAMPLES

The following examples are provided to better illustrate the claimed invention and are not to be interpreted as limiting the scope of the subject matter. To the extent that specific materials are mentioned, it is merely for purposes of illustration and is not intended to limit the invention. One skilled in the art may develop equivalent means, compositions or reactants without the exercise of inventive capacity and without departing from the scope of the present invention.

Example 1

Bioresponse Protein Polymers, Generally

ELPs are repeated pentameric peptides, (VPGX$_{aa}$G)$_n$ (i.e., n number of [SEQ ID NO. 19]). These peptides have characteristic inverse phase transition temperatures, T$_t$, above which they phase separate from aqueous solution. By choosing the identity of X$_{aa}$ and the length n, ELPs of different T$_t$ can be efficiently and precisely biosynthesized (Tables 1 and 2).

Genetically engineered ELPs are pharmacologically relevant, being monodisperse, biodegradable, and biocompatible. The present invention harnesses these features of bioresponsive protein polymers to control ocular clearance (FIG. 1B, C).

To reduce the frequency of dosing, lacritin has been genetically fused with ELPs of different transition temperatures that are above and below the ocular surface temperature (Table 2). One example fusion protein, lacritin-V96, is soluble at room temperature and administered to the eye, upon which the body temperature raises them above their transition temperature. This process induces the formation of adhesive ELP aggregates, which slows or prevents ocular clearance. Free, active lacritin is expected to be in equilibrium with the ELP aggregates and extends the period of treatment from a single drop. ELPs with a transition temperature greater than 37° C. are expected to clear quickly from the eye; however, ELPs with transition temperature between room temperature (25° C.) and body temperature (37° C.) are expected to drain slowly from the eye.

TABLE 1

Examples of of ELP protein polymers

| Label | Amino acid sequence | *MW (kD) | Target behavior in body | **Assembly temperature (° C.) | ***Hydrodynamic Radius at 37° C., R$_h$ = (nm) |
|---|---|---|---|---|---|
| I96 | G(VPGIG)$_{96}$Y [SEQ ID NO: 11] | 40.9 | microparticle depot | 20 | >>1,000 |
| S96 | G(VPGSG)$_{96}$Y [SEQ ID NO: 12] | 38.5 | soluble control | 56 | 4.2 ± 1.8 |
| S48I48 | G(VPGSG)$_{48}$(VPGIG)$_{48}$Y [SEQ ID NO: 13] | 39.6 | nanoparticle | 25 | 21.8 ± 1.5 |

*Molecular weight estimated for expressed gene product, as confirmed using MALDI-TOF mass spectrometry
**Assembly temperature determined using optical density at 350 nm on a temperature gradient of 1° C. min$^{-1}$
***Radii determined using dynamic light scattering at 25 uM ELP in phosphate buffered saline.

TABLE 2

Lacritin-ELP constructs evaluated

| Protein Name | **lacritin-ELP amino acid sequence | Approximate MW (kD) | *T$_t$ (° C.) | Expected ocular clearance |
|---|---|---|---|---|
| Lac-V96 [SEQ ID NO: 14] | MEDASSDSTGADPAQEAGTSKPNEEISGPAEPASPPETTTTAQETSAA AVQGTAKVTSSRQELNPLKSIVEKSILLTEQALAKAGKGMHGGVPG GKQFIENGSEFAQKLLKKFSLLKPWA-<u>GLVPR\|GS</u>-G[VPGVG]$_{96}$Y | 52.5 | 26.8 | slow |
| Lac-I96 [SEQ ID NO: 15] | MEDASSDSTGADPAQEAGTSKPNEEISGPAEPASPPETTTTAQETSAA AVQGTAKVTSSRQELNPLKSIVEKSILLTEQALAKAGKGMHGGVPG GKQFIENGSEFAQKLLKKFSLLKPWA-<u>GLVPR\|GS</u>-G[VPGIG]$_{96}$Y | 50 | 10 | fast |
| Lac-S96 [SEQ ID NO: 16] | MEDASSDSTGADPAQEAGTSKPNEEISGPAEPASPPETTTTAQETSAA AVQGTAKVTSSRQELNPLKSIVEKSILLTEQALAKAGKGMHGGVPG GKQFIENGSEFAQKLLKKFSLLKPWA-<u>GLVPR\|GS</u>-G[VPGSG]$_{96}$Y | 50 | 60 | fast |

*As observed for Lac_V96 and expected based on the approximate transition temperature for I96 and S96.
**Amino-terminal lacritin with the signal peptide removed followed by an underlined thrombin cleavage site, followed by a carboxy terminal ELP.

Example 2

Characterization of Lacritin-ELP Conjugate Assembly and Bioactivity

The inventors cloned (FIG. 3A) and purified lacritin-ELP conjugates (Table 2). One of these conjugates, Lac-V96, has been extensively characterized through proteolytic cleavage via thrombin. A purified ELP fusion proteins (Lac-V96), a purified ELP (V96), and the purified cleaved lacritin (Lac) are all depicted (FIG. 4A, 5A). The molecular mass for these constructs was confirmed using mass spectrometry (FIG. 4B, 5B, Table 3). The ELP lacritin fusion protein Lac-V96 was able to undergo temperature dependent phase separation (FIG. 6); furthermore, Lac-V96 is soluble at room temperature and phase separates above 30° C. More importantly, the inventors have applied this lacritin fusion protein to successfully induce expression of an enzyme marker associated with secretion, beta hexosaminidase, in primary cells isolated from rabbit lacrimal gland (LGACs).

Example 3

Constructing Genes Encoding for Lacritin-ELPs

Figure 10:
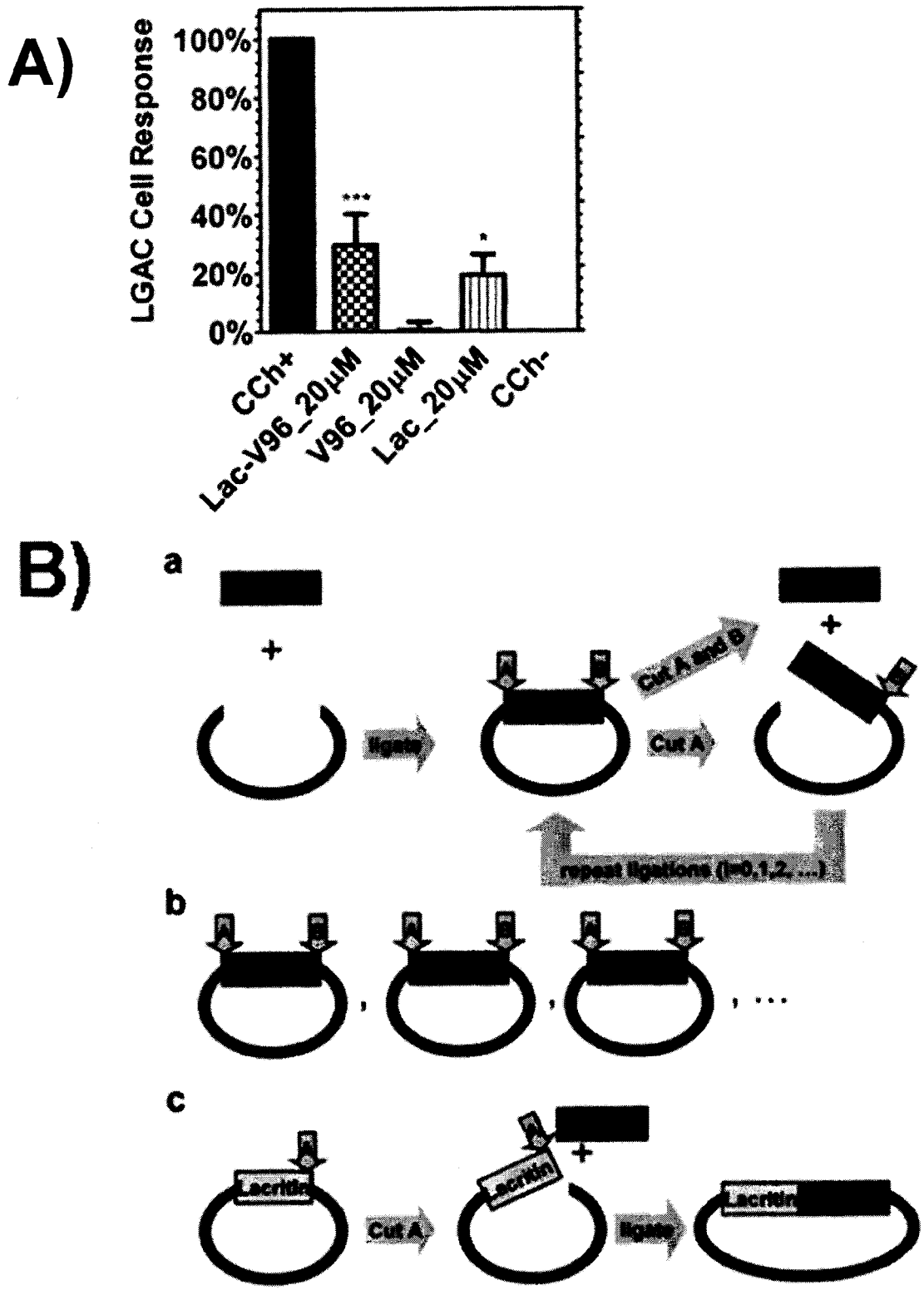
FIG. 10. Construction and Expression of a functional lacritin ELP fusion protein. (A): The lacritin constructs were evaluated for their ability to induce secretion of β-hexosaminidase from primary rabbit LGACs. Carbachol (CCH+) provided a positive control. Lac-V96 and Lac both have significantly (*p<0.05) more activity than the negative control (CCH−) or V96 alone. The similarity in efficacy between the isolated lacritin and ELP fusion protein suggests they may have similar activity; however, the phase behavior of the ELP domain may promote ocular retention and enhance activity in vivo. (B): Steps of recursive directional ligation. (Ba): ELP gene is inserted into the pet25b+ vector and dimerized by ligating with another ELP. It is cut at two sites with BseRI (RE-A) and AcuI (RE-B). A linearized gene of the ELP is obtained by cutting only at the A site. (Bb): The steps are repeated until the desired ELP chain length is obtained. (Bc): ELP is inserted into a plasmid containing the lacritin gene to form a lacritin ELP fusion protein.

Genetic engineering can be used to prepare repetitive polypeptides of specific chain length. In this approach, oligonucleotide cassettes encoding the monomer gene for the pentapeptide ELP is ligated into a specially modified cloning vector, such as pet25b+. Restriction enzymes are selected RE1 and RE2, which cleave the monomer genes as demonstrated in FIG. 10B. The cloning vector with the monomer gene is digested with both RE1 and RE2 to produce an insert, which is gel purified and ligated into a separate preparation of vector linearized by digestion with only RE1. This approach leads to the controlled dimerization of the synthetic gene. This technique can be repeated until an ELP of desired chain length is formed. After formation of a library of synthetic genes encoding ELPs of different lengths and guest residues ($X_{aa}$), selected ELPs are transferred onto a plasmid at an RE1 cut site to the carboxy terminus of a lacritin gene (FIG. 10B). Following every ligation, bacterial colonies are grown up in a 4 mL culture and harvested for plasmid DNA. The DNA is then screened by diagnostic digestion using XbaI and BamHI for the correct insertion of both the lacritin and ELP genes. Positive plasmids are then sent for DNA sequencing from the T7 promoter and terminator sequences, which is used to confirm the presence of a ribosome binding sequence, a start codon, an in frame lacritin gene, an in frame thrombin cleavage site, an inframe ELP, and an in frame stop codon. Successfully sequenced plasmids are then moved to expression bacterial cultures.

Example 4

Purification of Lacritin-ELP Fusion Proteins

Purified plasmids (FIG. 3A) are transferred into an expression host optimized for the production of repetitive sequences, the BLR(DE3)™ (Novagen). The inventors identified a critical production stage, whereby reducing the incubation temperature to 30 degrees Celsius for 24 hours is important to prevent premature cleavage of ELPs and lacritin. ELPs and lacritin-ELPs are purified using inverse phase transition cycling. Briefly, this method makes use of the ELP phase separation to induce selected precipitation of ELP fusion proteins using centrifugation. The phase transition temperature can be induced using a mild combination of 0 to 3 M NaCl and heating to temperatures up to about 37° C. This causes the phase separation of ELPs, which are centrifuged under about 10,000 g. The supernatant, which includes bacterial contaminants, is discarded. Next, the ELP pellet is cooled to 4° C. and agitated gently until it returns to solution. The redissolved ELP is again centrifuged to discard any remaining protein contaminants. As needed, this cycle of hot and cold centrifugation is repeated between 3 and 6 times to produce pure fusion constructs.

Example 5

Lac-ELPs and ELPs are Purified by Inverse Transition Cycling (ITC)

Figure 15:
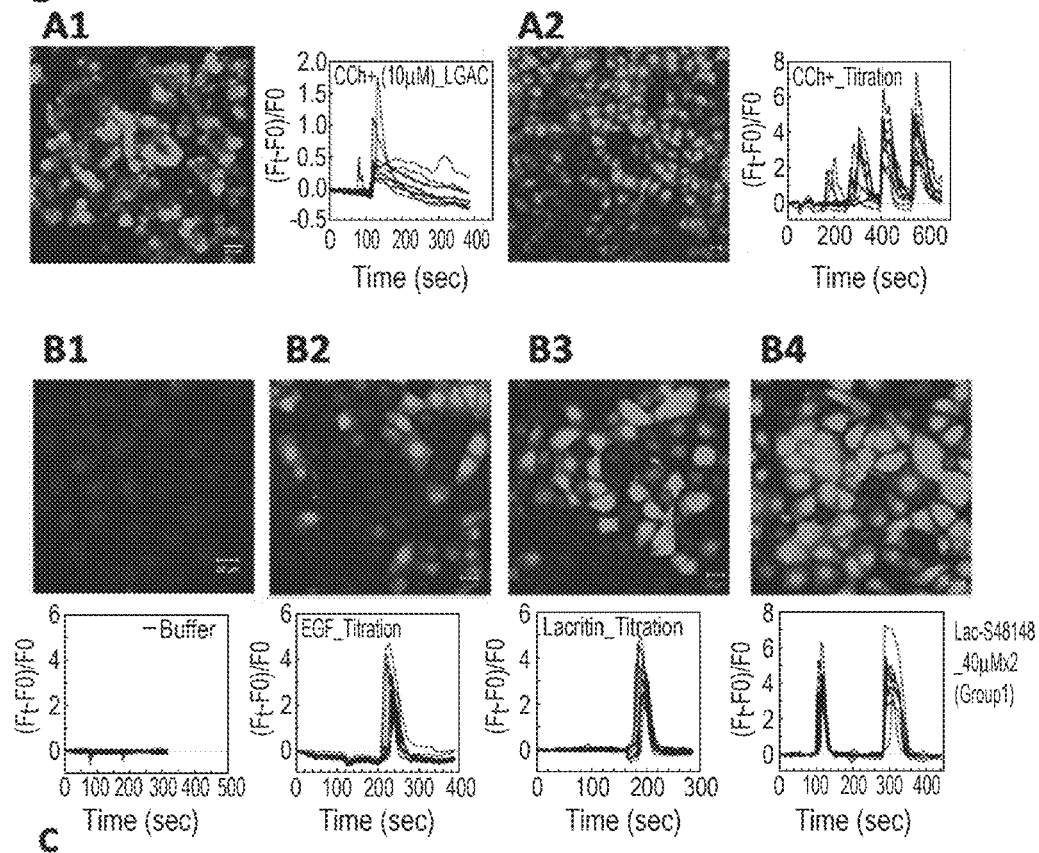
Figure 16:
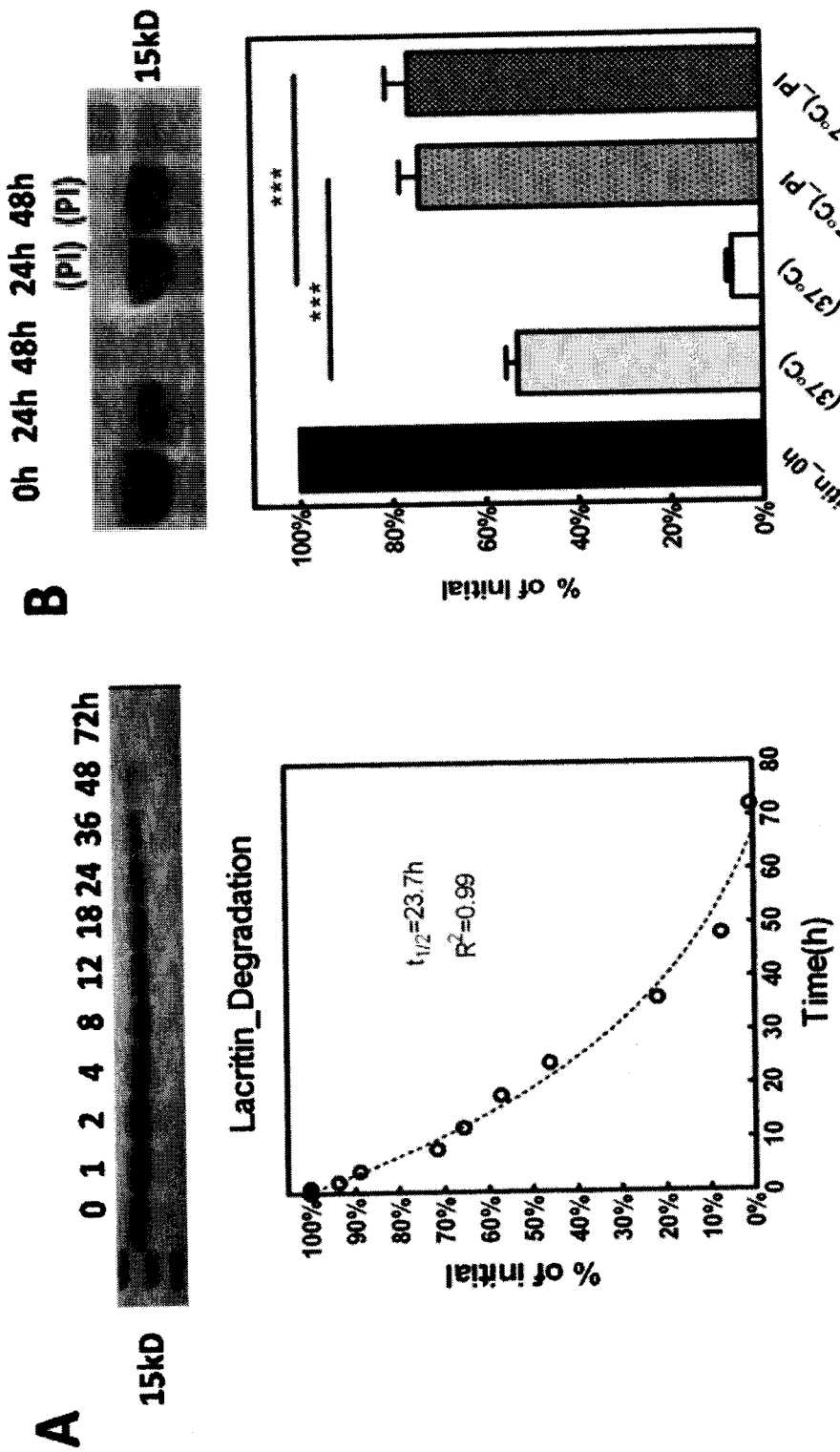
FIG. 16. Lacritin is susceptible to protease. (A): Time dependent degradation of purified lacritin. Up: SDS-PAGE stained with coomassie blue showing disappearing of lacritin band; lower: one-phase decay fitting curve of lacritin degradation, $t_{1/2}$=23.7 h ($R^2$=0.99). (B): Lacritin degradation can be inhibited by protease inhibitor cocktail. (C): Western blot of purified lacritin probed with anti-lacritin antibody. (D): MALDI-TOF analysis of lacritin degradation product. (E): Examples of possible cutting sites within lacritin sequence. *Truncation products following degradation were assigned by MALDI-TOF MS by comparison of measured with predicted mass to charge ratios (m/z) with +1 charge ionization ($[M+H]^+$). Corresponding sequences are shown. Bold and underlined sequence: Syndecan-1 binding site. Blue: residual thrombin cleavage site. Red: possible cutting site. ***p<0.001
Figure 16:
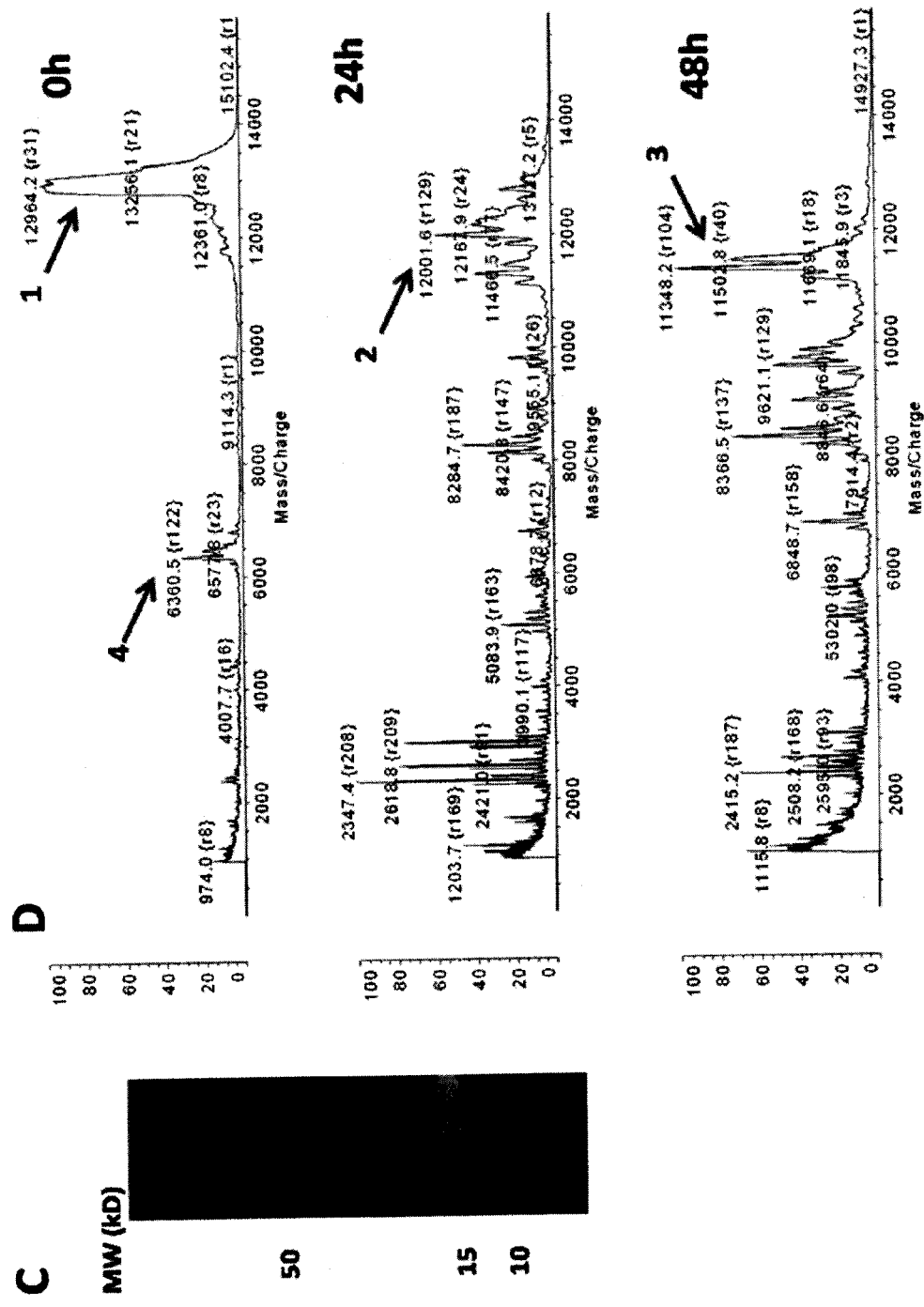

In another example of the versatility of bioresponse polymers, ELPs can used as purification tag to extract soluble fusion proteins from E. coli debris due to their unique reversible inverse phase transition behavior. Lacritin has been previously purified using intein system, which requires multiple steps of chromatography. The inventors herein describe an alternative purification approach using ELPs. With IPTG induction, Lac-I96, Lac-V96, Lac-S96 and Lac-S48I48 can achieve satisfactory yield of more than 40 mg/L. MALDI-TOF analysis and western blotting with anti-lacritin antisera further confirmed successful construction of Lac-ELPs (Figure FIG. 15C). Interestingly, after ITC purification, the inventors observed two major bands on SDS-PAGE of purified Lac-ELPs (FIG. 5A), upper band around 52 kD and lower band around 40 kD, which suggested there was pre-mature cleavage of lacritin from the fusion construct. Further degradation study confirmed this observation (FIG. 16A). The inventors utilized Superose size exclusion column to remove free ELP tags (FIG. 3B). Internal lacritin control was liberated from ELP tag via cleavage at designed thrombin recognition site encoded between the two moieties (FIGS. 1A and 2A). Similar to previous reports, lacritin ran higher on SDS-PAGE than expected M.W. 12 kD (FIGS. 4A and 5A).

Using above method, Lac-ELPs, ELPs and lacritin can reach more than 95% purity on SDS-PAGE stained with coomassie blue (FIGS. 4A and 5A) The inventors also noticed several smaller MW bands (around 10 kD) in purified lac-ELP and lacritin products (FIGS. 4A, 5A, and 8C). Analysis of MALDI-TOF data indicated that these difference size fragments released from lac-ELPs are multiple sites within the lacritin-thrombin region of the fusion protein may be susceptible to enzymatic attack by proteases or act as a protease itself (FIGS. 16D&E).

More specifically, ELPs I96, V96, S96 and S48I48 were expressed in BLR (DE3) E. coli cells (Novagen Inc., Milwaukee, Wis.). Briefly, after overnight start culture, protein was expressed for 24 h in an orbital shaker at 37° C. at 250 rpm. Cell culture were harvested and re-suspended in phosphate buffer saline (PBS). After sonication and removing insoluble cell debris and nucleic, ELPs were purified from clarified cell supernatant by inverse transition cycling (ITC)' as previous reported until ELP purity was determined to be approximately 99% pure by SDS-PAGE gels stained with $CuCl_2$.

Lac-ELPs were expressed in BLR (DE3) E. coli cells using IPTG induction. Briefly, after overnight starter culture, cell pellet was inoculated into 1 L TB medium and grew at 37° C. until OD600 nm reached 0.5. 500 ul of 1M IPTG stock solution was added into cell culture and temperature was decreased to 25° C. to optimize protein expression. After 5 h induction, cells were harvested and purified using ITC. Due to fast degradation of Lac-ELP, fusion protein was further polished by using Superose size exclusion column at 4° C. After balancing the column with PBS (Ph 7.4), 100 mg Lac-ELP was then loaded onto the column and washed out by isocratic flow of PBS at 0.5 ml/min. Peak 1 was collected and concentrated using Amicon Ultra 10 Kd. Free lacritin is released by thrombin cleavage of Lac-ELP fusion protein. Briefly, 300 ul thrombin beads slurry (Sigma-Aldrich) was added into 200 mg ITC purified Lac-ELP and incubated at room temperature for overnight. After pelleting down thrombin beads at 2,500 rpm, solution was warmed up to 37° C. and centrifuged at 4,000 rpm for 10 min to remove phase transitioned ELP tag. Supernatant after spin was concentrated using Amicon Ultra 3 Kd. Protein concentrations were determined by UV-visible spectroscopy at 280 nm ($\delta ELP=1285M^{-1}$ $cm^{-1}$, $\epsilon Lac\text{-}ELP=6990M^{-1}$ $cm^{-1}$, $\epsilon Lac=5500M^{-1}$ $cm^{-1}$). Protein molecular weight is further confirmed by MALDI-TOF analysis.

Example 6

Assessing the Purity and Molecular Weight for ELP Fusion Proteins

Purified proteins were further characterized by SDS-PAGE and MALDI-TOF analysis. The temperature-dependent phase transition behavior of both ELPs and Lac-ELPs was characterized by measuring the optical density at 350 nm (OD350 nm) as a function of solution temperatures between 15 and 85° C. in a DU800 UV-visible spectrophotometer.

More specifically, ELP and ELP fusion proteins, are run on a standard SDS-PAGE apparatus. ELPs on PAGE can be stained and imaged using copper chloride. In addition to purified ELP and ELP-lacritin, thrombin can be added to the fusion proteins. After incubation under standard conditions, this process liberates the free lacritin (FIGS. 1A, 2A, 4A and 5A). Although lacritin is approximately 12 kDa, it is has been reported to run on PAGE as a band around 18 kDa, which was observed by the inventors. The resulting gel depicts the purity of the peptides purified using ELP phase separation (FIGS. 4A and 5A).

Further confirming the identity of these gene products, the specific protein spots are isolated and characterized using matrix assisted laser desorption ion time of flight mass spectrometry (MALDI-TOF) (FIGS. 4B and 5B). The resulting masses are consistent with the expected protein mass to a high degree of accuracy (Table 3).

TABLE 3

MALDI-TOF analysis of purified ELP and lacritin fusion proteins

| Protein | Expected Mass (kD) | MALDI-TOF result (kD) |
| --- | --- | --- |
| Lac-V96 | 52.52 | 52.29 |
| V96 | 39.55 | 39.21 |
| Lac | 12.85 | 12.73 |

Example 7

Measurement of Phase Transition Temperature for ELP Fusion Proteins

ELP transition temperatures are determined on a Beckman DU800 UV-VIS spectrophotometer under a temperature gradient of 1° C. per minute in PBS. The transition temperature, by turbidometric analysis, is defined as the maximum first derivative of the optical density at 350 nm. ELP transition temperatures are functions of the logarithm of concentration; therefore, a range of sample concentrations from 5 to 100 μM ELP are typically observed and fit to the following equation:

$$T_t = m \, Log_{10}[C_{ELP}] + b$$

Where $C_{ELP}$ (μM) is the ELP concentration, m is the slope (° C. per $Log_{10}$[μM], and b (° C.) is the transition temperature at 1 μM. The transition temperatures for an ELP with and without fusion to a lacritin protein domain are indicated, which demonstrate that there is a measurable, but minimal decrease in the transition temperature (FIG. 8A-D). Further, it is observed that lacritin undergoes degradation at 37° C. (FIG. 7A-C).

Typically, PBS solutions of protein sample (100 μM, 50 μM, 25 μM, 10 μM and 5 μM) were heated at 1° C./min between 10° C. and 85° C. $T_t$ under each concentration is defined as the maximum first derivative of turbidity change. Particle size distribution of Lacritin, ELP and Lac-ELP fusions was measured as a function of temperature increase by dynamic light scattering (DLS). Briefly, protein samples were prepared at 25 μM in PBS and filtered through a 20 nm filter (Whatman Anodisc) at 4° C. Autocorrelation functions were collected using a DynaPro-LSR dynamic light scattering Wyatt Plate Reader (Wyatt Technology, Santa Barbara, Calif.). Light scattering data were collected at regular temperature intervals (1° C.) as solutions were heated from 5 to 60° C. The results were analyzed using a Rayleigh sphere model and fitted into either a regularization or cumulant algorithm based on the sum-of-squares value. Critical micelle temperature (CMT) for each protein construct was defined as the lowest temperature at which the Rh is significantly greater than the average monomer Rh.

Example 8

Lacritin Moiety Influences Phase Transition Behavior of Parent ELPs

Figure 8:
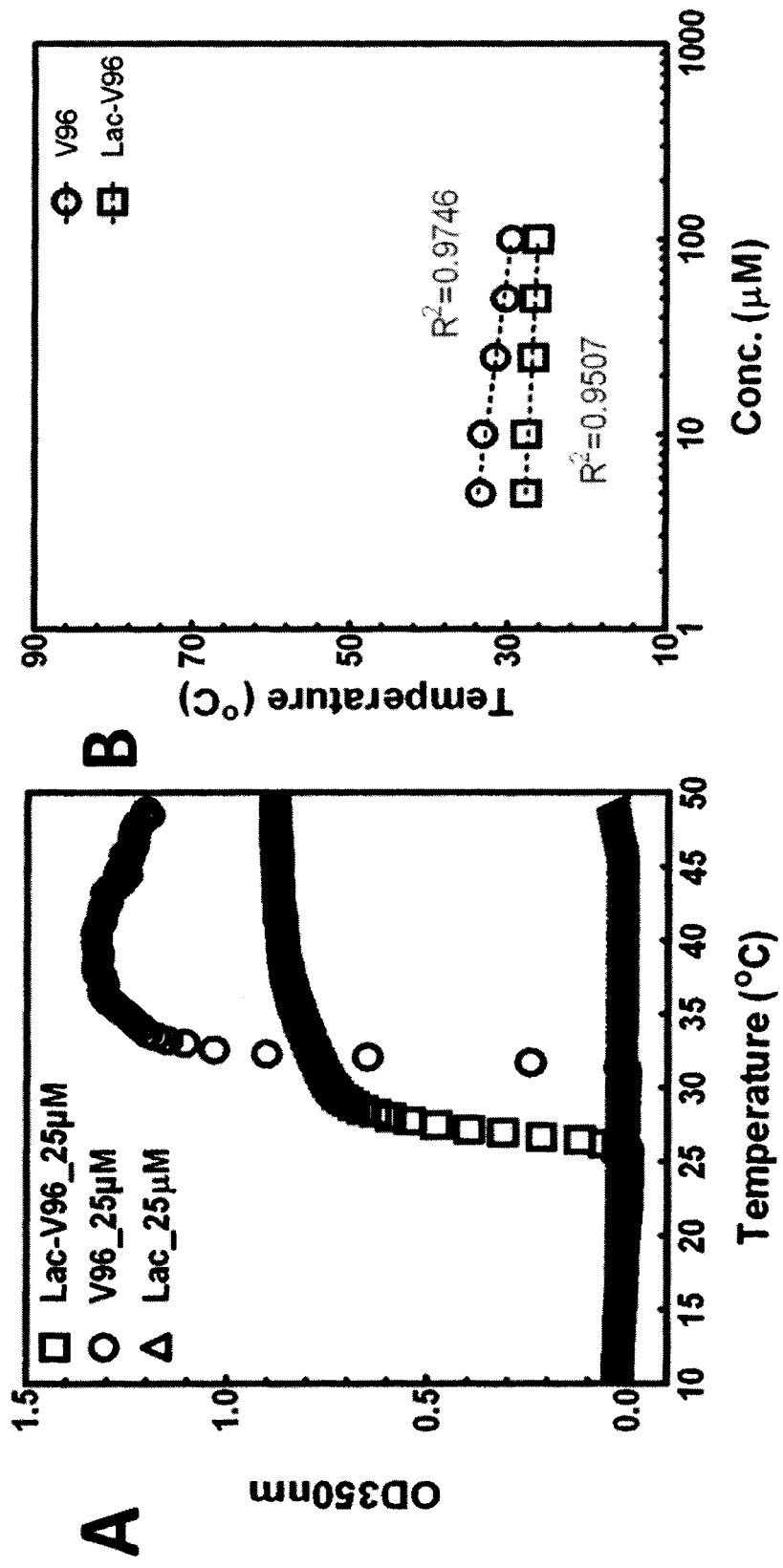
FIG. 8. Lacritin influences inverse phase transition behavior of parent ELPs. (A): Representative phase transition turbidity change observed at 350 nm (OD350 nm) as a function of solution temperature for Lac-V96 (open circles), V96 (open squares) and lacritin (open triangle) at 25 µM. (B, C&D): $T_t$ as a function of concentration (100 µM, 50 µM, 25 µM, 10 µM, 5 µM) for Lac-ELP and ELPs in PBS. Data points were fit into model: $T_t$=m Log 10[CELP]+ b, where CELP (µM) is the ELP concentration, m is the slope (° C. per Log 10[µM], and b (° C.) is the transition temperature at 1 µM. R2 and 95% confidence interval of fitting was shown in red. * (B): S96 and Lac-S96. (C): V96 and Lac-V96. (D): I96 and Lac-I96, E: S48I48 and Lac-S48I48.
Figure 8:
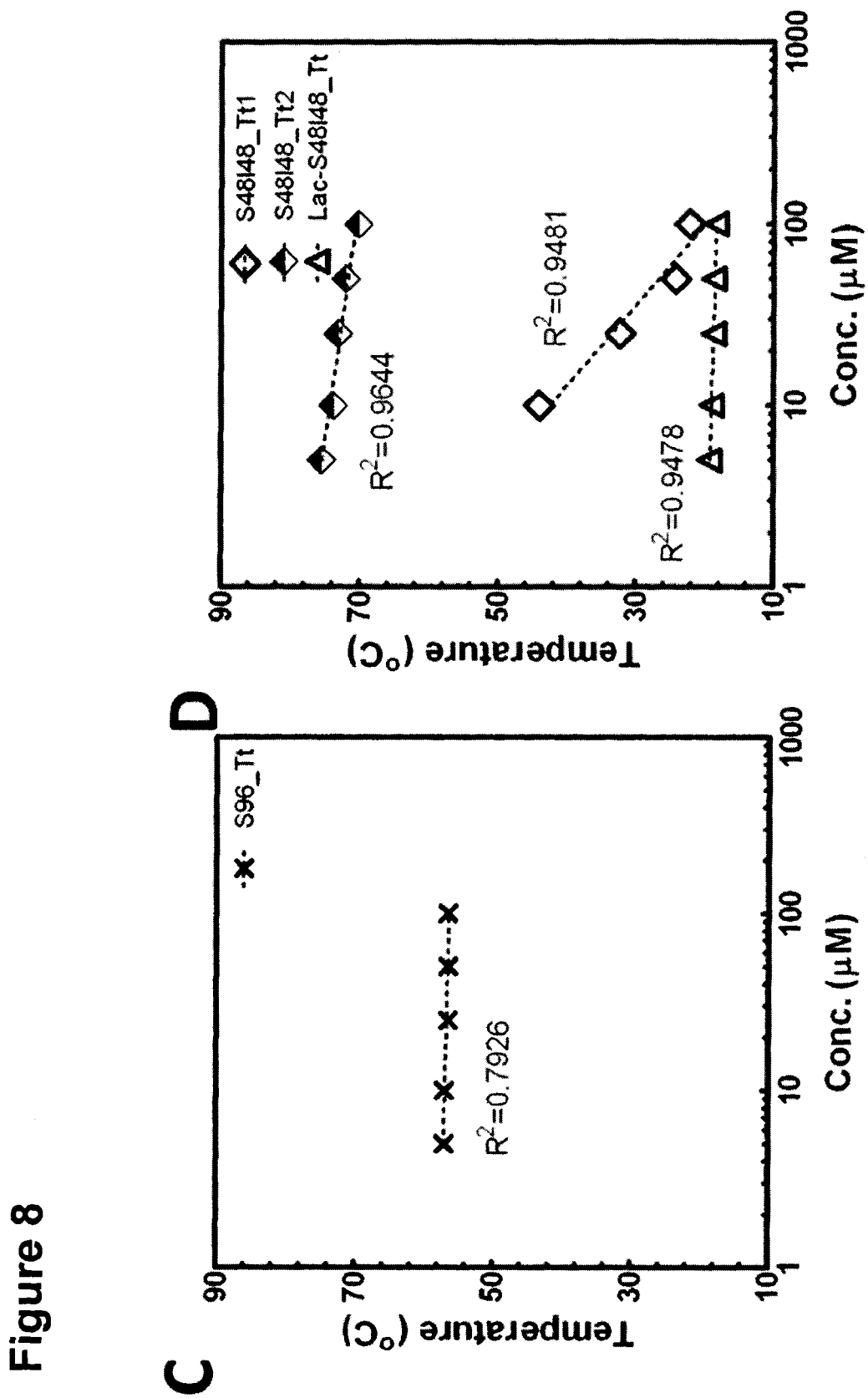

As ELP fusion protein, Lac-ELP would be expected to undergo phase transition like parent ELPs, one can characterize the influence of fusion lacritin moiety on Tt of attached ELPs. FIG. 2B and FIG. 8 showed inverse phase transition characterization of all expressed ELPs and lac-ELP fusion proteins at a concentration of 5, 10, 25, 50 and 100 μM in phosphate buffered saline (PBS) over the experimentally accessible temperature range of 10-90° C. As described, Tt of ELPs could be predicted by a simple equation, which accounts for the ELP concentration and its length: Tt=m Log 10[CELP]+b, where CELP (μM) is the ELP concentration, m is the slope (° C. per Log 10 [μM]), and b (° C.) is the transition temperature at 1 μM. Comparison of lacritin, Lac-V96 and V96 phase transition curve at 25 μM (FIGS. 8A and 8B) demonstrated maintenance of the phase transition behavior of parent ELPs.

However, a 5° C. decrease in Tt at 25 μM was observed for the fusion protein. Interestingly, ΔTt of Lac-S48I48 and Lac-S96 was much more dramatic compared to S48I48 and S96 (FIGS. 8C and 8D). While S48I48 exhibited one smooth micelle formation and one sharp bulk phase transition, only one sharp phase transition around 15° C. was noticed with Lac-S48I48, which was 60° C. lower than bulk phase transition temperature of S48I48 (FIG. 8D). On the contrary, Lac-S96 completely abolished phase transition behavior of parent S96 within accessible temperature range of 10-90° C. (FIG. 8C).

Example 9

Lac-ELPs Pre-Assemble into Nano-Sized Particles

Figure 9:
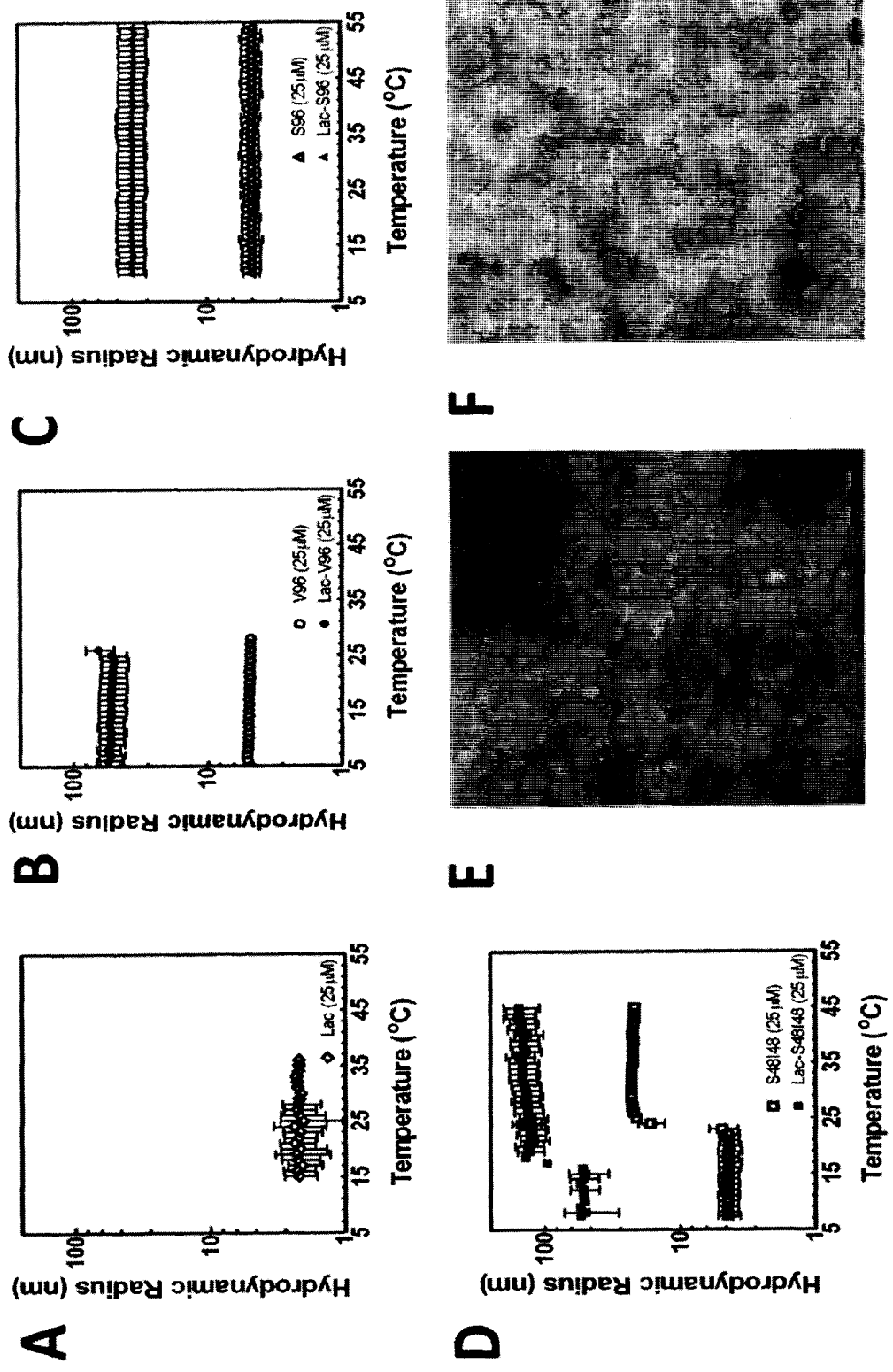
FIG. 9. Lac-ELPs assemble into nanoparticles at low temperature. (A): Free lacritin exhibited as 2-3 nm monomers within experiment temperature range. (B): V96 stayed as 2-3 monomers until bulk phase transition; Lac-V96 preassembled into 30-40 nm particles below $T_t$ and aggregated into micron-sized coacervate above Tt. (C): As soluble ELP control, S96 remained as 2-3 nm monomers between 10° C. and 55° C. while Lac-S96 assembled into 30-40 nm particles within same temperature range. (D): S48I48 existed as soluble monomers and aggregated into stable monodisperse nanoparticles with a Rh of 20-30 nm above its CMT (26.6° C.). Lac-S48I48 preassembled into 30-40 nm particles similar to other Lac-ELPs; above its $T_t$, Lac-S48I48 further reconstituted into 130-140 nm micelles. (E&F): TEM images of S48I48 and Lac-S48I48 micelles, with average diameter of 36.5±5.8 nm and 67.1±11.5 nm accordingly. (G): Cartoon showing S48I48 and Lac-S48I48 micelles. (H&I): Cryo-TEM images of S48I48 and Lac-S48I48 micelles, with average diameter of 29.1±3 0.4 nm and 56.7±3.1 nm accordingly. *Hydrodynamic radius (Rh) of lacritin, Lac-ELPs and parent ELPs were measured at 25 µM in PBS (pH. 7.4) as a function of temperature by DLS.

Phase transition characterization results suggested the fusion lacritin moiety may interact with each other in a random/organized pattern other rather simply staying as monomers. One can further characterize the self-assembly property of purified Lac-ELPs using Dynamic Light Scattering (DLS). As shown in FIG. 9A, free lacritin exhibited as 2-3 nm monomers between 5° C. and 60°. While S96 stayed stable as 2-3 nm monomers within experimental temperature range, Lac-S96 pre-assembled as 30-40 nm particles (FIG. 9C). Lac-V96 and Lac-I96 similarly exhibited as 30-40 nm pre-assembled particles until bulk phase transition above Tt (Figure (B). S48I48 was chosen as our micelle scaffold. Remarkably, as different from sharp phase transition of I96 and V96 below 37° C., S48I48 assembled from 2-3 nm monomers into 20 nm micelles above its critical micelle temperature (CMT) at around 26° C. (FIG. 9D). Same as other Lac-ELPs, Lac-S48I48 preassemble into 30-40 nm particles even at 5° C. As temperature was raised, Lac-S48I48 aggregated into 140-150 nm mono-dispersed particles above its Tt (FIG. 9D). Interestingly, native ELPs by themselves do not preassemble as their fusion constructs.

The DLS observations were further supported by high-resolution TEM and Cryo-TEM images of the corresponding nanoparticles. While S48I48 formed perfect micelle structure (FIGS. 9E&H), Lac-S48I48 presented a much larger size in its nanostructure, which was around 60-70 nm in diameter (FIGS. 9F&I). Discrepancy of micelles diameter measured using three techniques may come from the hydrophobicity of the fusion protein. As DLS measures hydrodynamic radius of the particle, lacritin moiety may exist in its most extended conformation in the solution and thus gave a 130-140 nm Rh reading. Both TEM and Cryo-TEM measured dry samples so that only the most hydrophobic core was shown in the figures. Due to fast degradation of Lac-S48I48, both TEM and Cryo-TEM images of Lac-S48I48 also showed partially degraded product: S48I48 micelles.

Example 10

Figure 12:
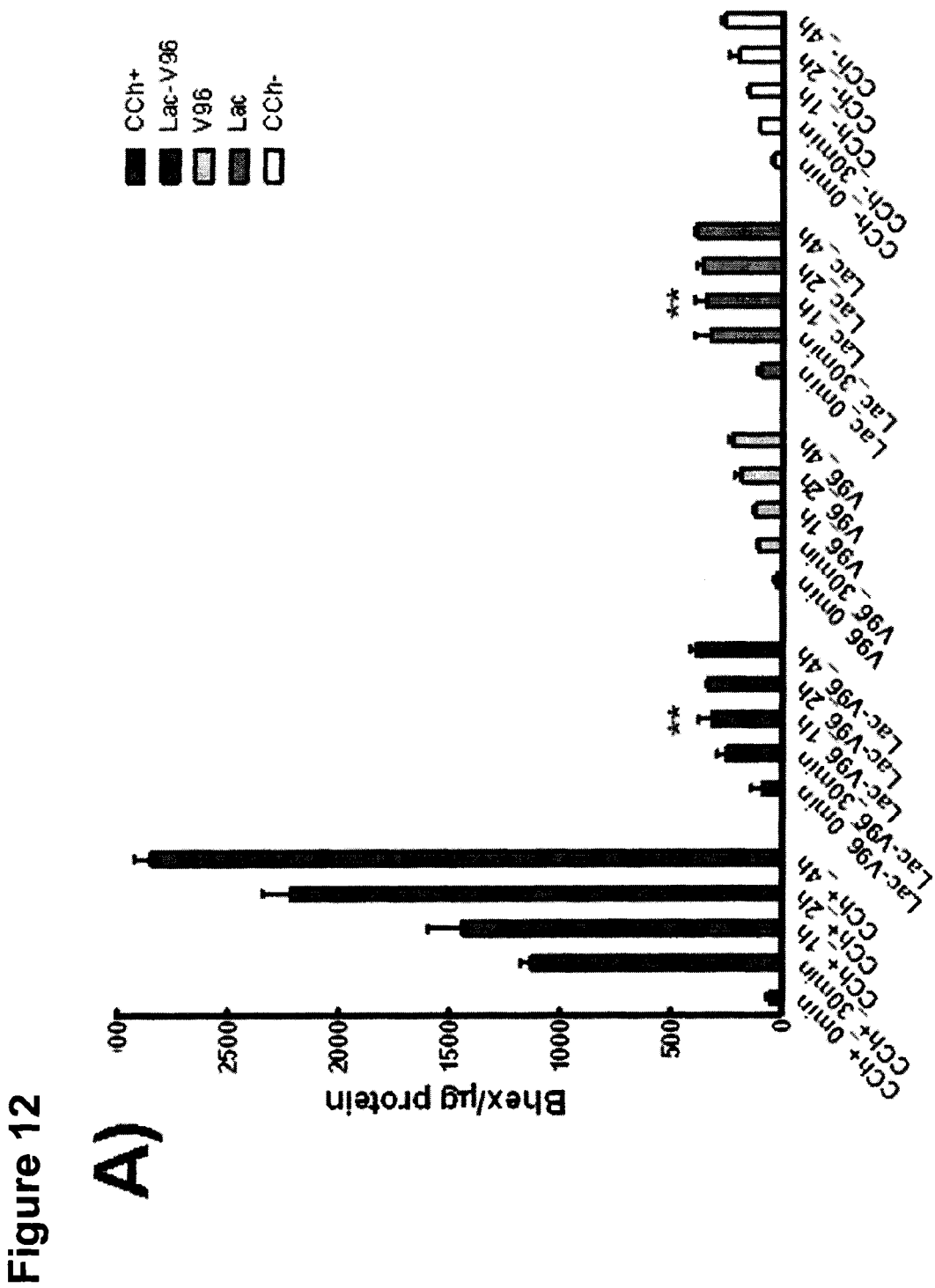
FIG. 12. Lacritin and Lac-ELPs stimulate β-hexosaminidase secretion in a time and dose dependent manner. β-hexosaminidase secreted into the supernatant culture media was measured by its catalytic activity against substrate 4-methylumbelliferyl N-acetylb-D-glucosaminide (4MUGlcNAc). Activity was normalized to OD465 nm/µg protein using BCA assay. Results from three individual cell preparations were analyzed. Each treatment was triplicated under every preparation. Figure was shown as cell response % compared to Carbachol stimulation and plain medium treatment. Significance was analyzed using two-way ANOVA. (A): LGACs were treated with 20 µM, 10 µM, 1 µM and 0.1 µM of Lac-V96, lacritin, V96 or controls for 1 h at 37° C. 10 µM and 20 µM Lac-V96 and lacritin significantly enhanced β-hexosaminidase secretion compared to V96 group, showing 20-30% LGAC response of positive control carbachol group. (B): LGACs were treated with 10 µM Lac-V96, lacritin, V96 or controls for 0 min, 30 min, 1 h, 2 h and 4 h. Lac-V96 and lacritin started stimulating β-hexosaminidase secretion as early as 30 min and reached a plateau at 1 h.
Figure 12:
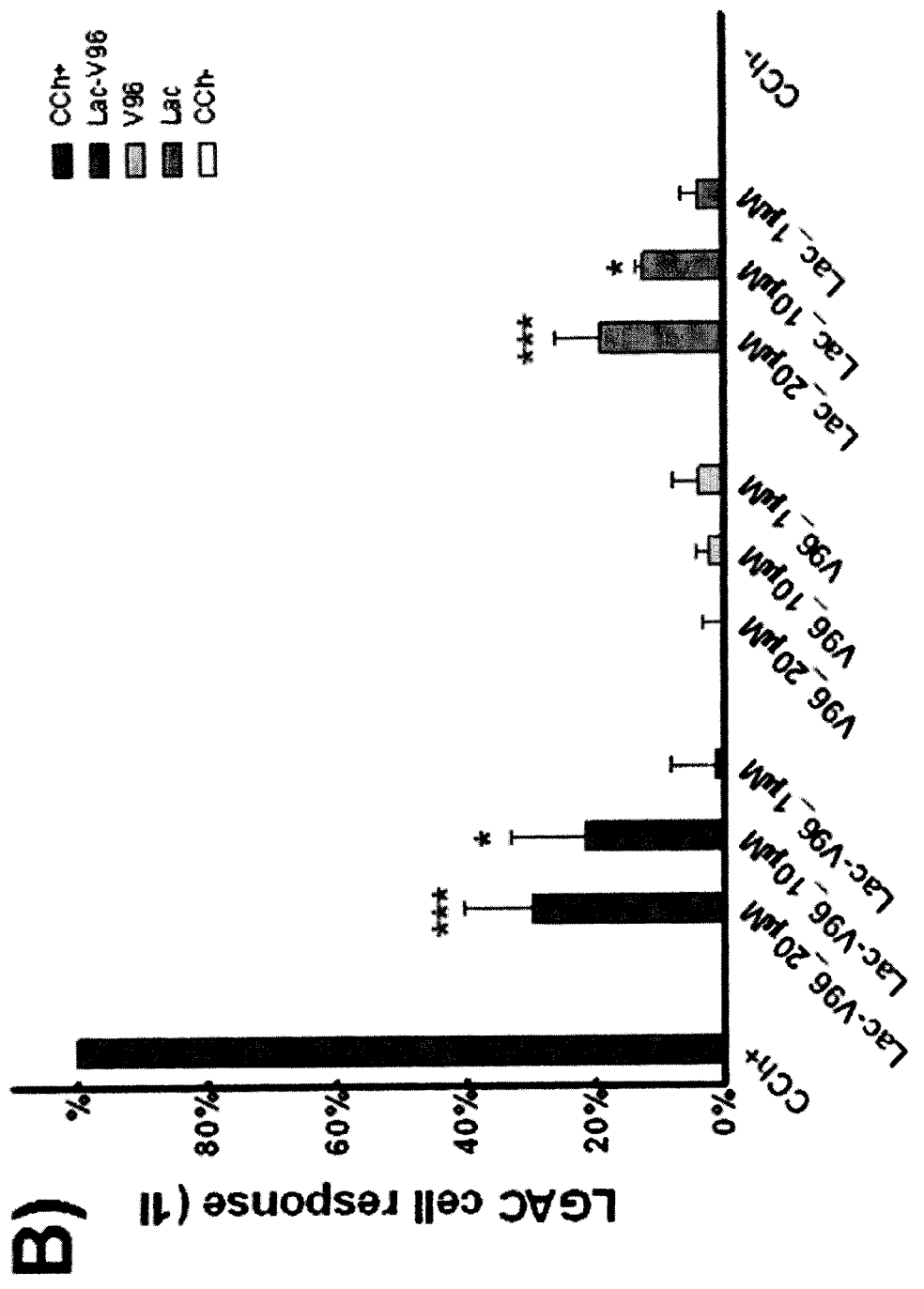

Measurement of Secretion of Beta Hexosaminidase from Primary Lacrimal Gland Cells Primary rabbit lacrimal gland acinar cells (LGAC) are used for in vitro secretion assay. Lacrimal acini were isolated and cultured for 2-3 days. Cells prepared in this way aggregate into acinus-like structures; individual cells within these structures display distinct apical and basolateral domains and maintain a robust secretory response. Total protein is quantified by Biorad assay and secreted protein is quantified by β-hexosaminidase assay. Briefly, primary rabbit acinar cells are seeded in 12-well plate 2 days before test. 2 hours before testing, old medium is replaced by 600 ul fresh PCM. Medium and cells are incubated at 37° C. for 2 hours. After collecting a sample of medium before secretion, ELP or lacritin ELP in PBS is added into each well and incubated at 37° C. for 30 min. All the samples are aggressively vortexed and centrifuged at 4° C., 12,000 rpm for 5 min. For Biorad assay, before and after secretion media samples are tested on 96-well plates in triplicate. For measurement of the β-hexosaminidase activity, 4-methylumbelliferyl N-acetyl-β-D-glucosaminide is used as a substrate in triplicate. Carbachol is used as a positive control for secretion; furthermore, specific secretion is normalized to the controls with and without carbachol (CCh+, CCh−) (FIGS. 10A and 12). The results show that ELP-lacritin retains biological activity in an physiologically relevant cell type, as demonstrated by changes in secretion of proteins delivered via Ad-Syn-GFP or LifeAct-RFP reporter constructs transfection into LGACs (FIG. 13). Changes in luminal regions and secretory vesicles was observed following ELP-lacritin and LAC administration. These results were further confirmed via direct measurement of protein secretion assays of rabbit LGACs, following ELP-lacritin and LAC stimulation (FIG. 12).

Example 11

Lac-ELPs and Lacritin Stimulate β-Hexosaminidase Secretion in Rabbit LGACs in a Time and Dose Dependent Manner In another example, a well-established in vitro rabbit LGAC secretion model to evaluate prosecretory function of lacritin and its Lac-ELP fusion constructs. FIG. 11 summarizes the β-hexosaminidase secretion results of acute Lac-ELPs and lacritin stimulation on rabbit LGACs. As internal positive control, 100 μM carbachol significantly stimulated secretion during the 4 h treatment time range. Compared to V96, Lac-V96 and lacritin significantly stimulated secretion at a concentration of 10 μM ($p<0.01$) and 20 μM ($p<0.001$) (FIG. 11A); apparent effects at 104 and 0.1 μM were not statistically significant. When treating LGACs with Lac-V96 and lacritin for 0-4 h at a concentration of 10 μM, significant secretion effect was observed after 30 min treatment and reached the peak at 1 h ($p<0.0001$); after 1 h, β-hexosaminidase secretion slower down (FIG. 11B). The inventors further compared LGACs response to Lac-ELPs with different hydrophobicity and conformation. While difference between Lac-I96 and Lac-V96 groups were marginal, Lac-S96 group exhibited a slight higher β-hexosaminidase secretion level and Lac-S48I48 group showed lowest response. This difference may come from the NGSEFAQKLL residues of lacritin sequence which is required for Syndecan-1 binding, which is believed to be crucial in downstream signal transduction. Since Lac-S96 is in its most soluble and extended conformation at 37° C. (FIG. 8C), no downstream protein-protein binding was blocked by the ELP tag. Due to phase transition at 37° C., Lac-I96 and Lac-V96 formed micron-sized coacervates (FIG. 8B), so that binding of lacritin to Syndecan was not as efficient. The most interesting result comes from Lac-S48I48. Though it did form micelle with lacritin on the corona as designed (FIG. 8D & FIG. 9), this construct showed the least activity. It is possible that NGSEFAQKLL residues at the C-terminus of lacritin were buried in the inter-section of micelle, which made them difficult to be recognized by the receptors.

Example 12

Lac-ELPs and Lacritin Stimulate Chronic F-Actin Remodeling Around LGAC Lumen and Enhanced Secretory Vesicle Formation In response to secretagogues, LGACs exocytose the contents of mature secretory vesicles containing tear proteins at their apical membranes into lumen area. Spurred by understanding the cellular mechanism of Lac-ELP and lacritin triggered secretion, the inventors utilized live LGACs time-lapse confocal fluorescence microscopy imaging to investigate changes of actin filaments located beneath the apical membrane during exocytosis evoked by Lac-ELP and lacritin (20 µM). For live cell imaging, rabbit lacrimal acini seeded on Matrigel-covered glass-bottomed round 35 mm dishes (Mat-Tek, Ashland Mass.) at a density of 4×10$^6$ cells per dish for 2 days were co-transduced with Ad-Syn-GFP and Ad-LifeAct-RFP at MOI of 6 for each for 2 hours. Cells were then rinsed and cultured in fresh medium for overnight to allow protein expression. Dual transduction efficiency (as measured by RFP-actin expression) ranged from 80-90% in each experiment. On day 3, lacrimal acini were analyzed by time-lapse confocal fluorescence and DIC microscopy using Zeiss Multiple Time Series V3.2 software modules. Live cell analyses were performed at 37° C. For time-lapse analysis, acini of similar size (4-6 cells arranged around a central lumen) were chosen. DIC images and RFP, GFP fluorescence were acquired simultaneously using the 488 line of the Argon Laser.

Similar to other epithelial cells, actin filaments in LGACs are primarily enriched beneath the apical plasma membrane and less abundant beneath basolateral membranes. Here, the inventors transduced LGACs with high efficiency (80-90%) replication-defective adenovirus (Ad) encoding RFP-actin (Ad-LifeAct-RFP) to label the actin filament array in lacrimal acini and measured its dynamics change during stimuli. Adenovirus encoding cytosolic protein Syn-GFP (Ad-Syn-GFP) was double transduced. Images obtained for different treatments were shown for plain PCM medium/CCh– (FIG. 14B), carbachol (100 µM) and Lac-V96 (20 µM). Image acquisition of treated acini was initiated 30-60 seconds after treatment addition, due to the time required to refocus. In the absence of any treatment, there was little global remodeling of apical or basolateral actin filaments; only subtle basal release of a few SVs at the apical membrane were detected (FIG. 14B CCh–). While positive control carbachol (100 µM) acutely (0-15 min) increased significant apical actin filament turnover and promoted transient actin assembly around apparent fusion intermediates (FIG. 14B CCh+); Lac-V96 (20 µM) exhibited a milder and more chronic effect on LGAC morphology change (FIG. 14B Lac-V96 (20 µM). After a lag time for about 20 min, 2 types of significant cellular changes were observed in LGACs perfused by Lac-V96: (1) increased irregularity in the continuity of apical actin filaments and formation of actin-coated structures beneath the apical and also basal membrane (purple arrows).

Example 13

Figure 14:
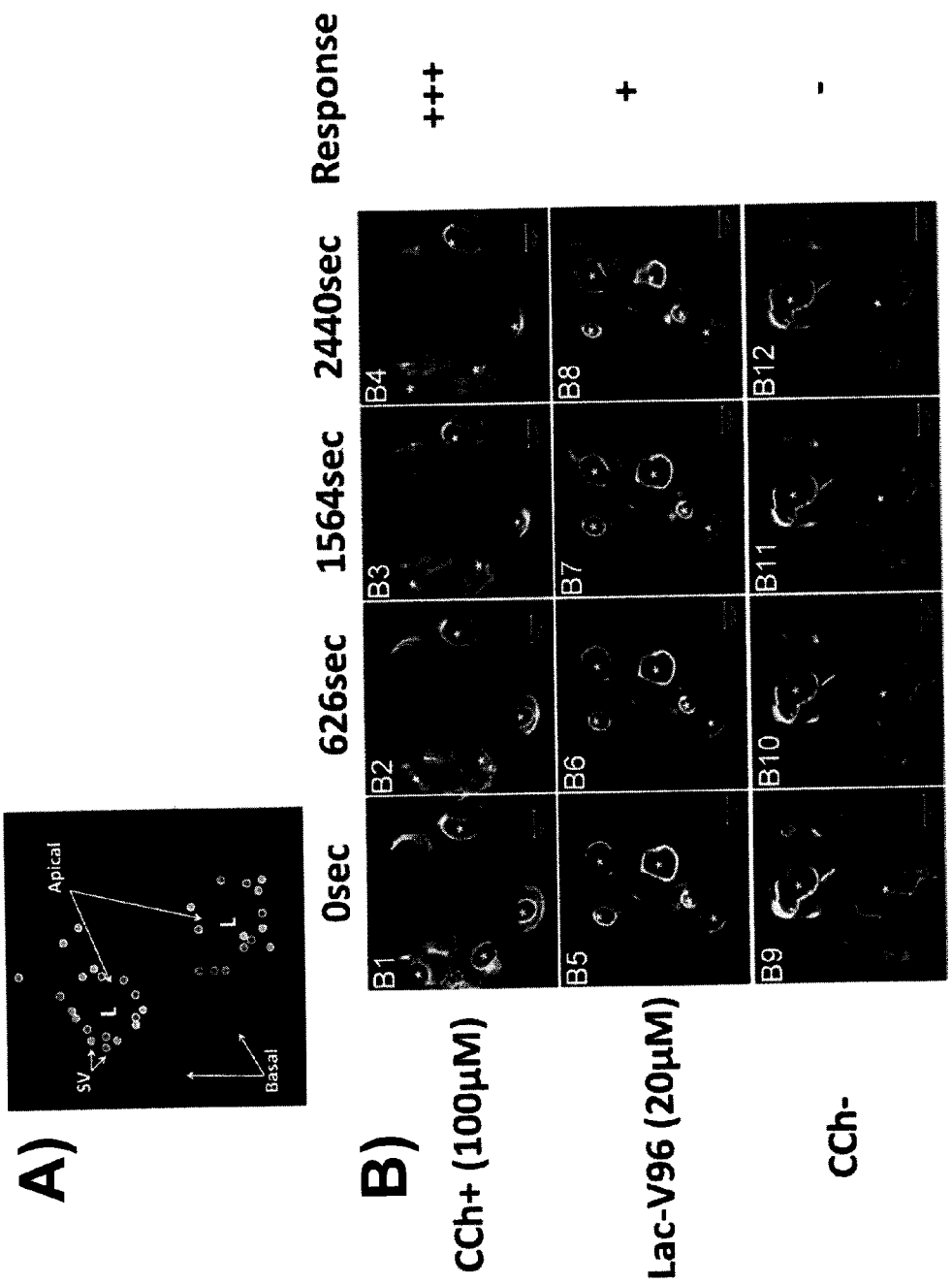
FIG. 14. Lac-V96 induces chronic Syn-GFP secretion and F-actin remodeling LGACs were transduced with adenovirus Ad-Syn-GFP and Ad-LifeAct-RFP to investigate the changes in secretion marker protein Syncollin-GFP (green) secretion and actin filaments (red) located beneath the apical and basal membrane during exocytosis evoked by the Lac-V96 and lacritin using time-lapse confocal fluorescence microscopy. (A): Structure model of LGAC. F-actin are more enriched underneath apical membrane. (B): While positive control muscarinic agonist carbachol (100 µM) acutely (0-15 min) increased significant apical actin filament turnover and also promoted transient actin assembly around apparent fusion intermediates (B1-B4); Lac-V96 (20 µM) exhibits a much milder and chronic effect on LGAC morphology (B5-B8). However, one can still observe increased irregularity in the continuity of apical actin filaments and formation of actin-coated structures beneath the apical and also basal membrane (purple arrows). The lumenal regions in LGACs were distinguished by *. L: lumen; SV: secretion vesicle FIG. 15. Lac-ELPs and lacritin triggers transient cytoplasmic Ca2+ wave in HCE-T cells but not in LGACs. (A1): Acute stimulation with carbachol (10 µM) induced Ca2+ oscillation in LGACs. (A2): Carbachol titration (0.4 µM, 1 µM, 10 µM, 100 µM, 1 mM and 1 mM) triggered concentration dependent Ca2+ wave in HCE-T cells. (B1): NaCl Ringer solution did not trigger Ca2+ wave in HCE-T cells. (B2&B3): EGF (10 ng/ml) or lacritin (10 µM) triggered 3-4 fold intracellular Ca2+ increase in HCE-T cells. (B4): Lac-S48I48 (40 µM×2) triggered 4-6 fold intracellular Ca2+ increase in HCE-T cells. (C): Summary of Ca2+ response in LGACs and HCE-T cells induced by treatment. *Fluorescence intensity change in ten individual cells were analyzed and plotted as (Ft−F0)/F0. Representative maximum cell response images were shown. HCE-T cells were rinsed twice with dPBS ($Ca^{2+}$ and $Mg^{2+}$ free) and incubated at 37° C. for 20 minutes in fresh KSFM medium without BPE or EGF containing 2.5 μM Fluo-4 AM. The cells were then rinsed twice with NaCl Ringer buffer (145 mM NaCl, 5 mM KCl, 1 mM CaCl2, 1 mM KH2PO4, 1 mM MgCl2, 10 mM glucose, and 10 mM HEPES, osmolarity 300, pH 7.4) and kept in the same buffer at room temperature for 30 minutes. For $Ca^{2+}$ free medium, 1 mM $Ca^{2+}$ was replaced with 0.5 mM EGTA. The data are presented as percentage change in fluorescence intensity at each time point ($F_t$) to the first time point ($F_0$) reading: ($F_t$−$F_0$)/$F_0$×100%.

Lac-ELPs and Lacritin Triggers Transient Cytosolic Ca2+Wave in HCE-T Cells but not LGACs The ability of actin filaments to remodel rapidly in response to changes in intracellular signaling is essential for their participation in exocytosis. Results from β-hexosaminidase secretion and confocal imaging studies show that Lac-ELP and lacritin trigger different cellular response compared to carbachol (FIGS. 11 and 14). Moreover, our β-hexosaminidase secretion result shows the minimal therapeutic concentration of lacritin is 10 µM, which is more than 100 fold of previous reported 10-100 nM dose required for peroxidase secretion. Without being bound by any particular theory, different receptor expression levels on rabbit and rat LGACs, may display differences in early signal transduction pathway participating in Lac-ELPs/lacritin triggered secretion. In the lacrimal gland, cholinergic agonists stimulate protein secretion by activating phospholipase C to break down phosphatidylinositol bisphosphate into 1,4,5-inositol trisphosphate (1,4,5-IP3) and diacylglycerol (DAG). 1,4,5-IP3 causes release of Ca2+ from intracellular stores. This Ca2+, perhaps in conjunction with calmodulin, activates specific protein kinases that may be involved in secretion. As a positive control used in this study, carbachol triggered intracellular Ca2+ wave in LGACs at an optimal concentration of 10-100 µM (FIG. 15A1). Supramaximal concentrations of carbachol caused a decreased response (data not shown). Ca2+ intensity elevated around 50-100%, with 50% of total acini responded to the stimuli. Although small intra-acini variance was observed, reflecting as a different Ca2+ intensity change, all acini responded to exogenous carbachol simultaneously in a twinkling scintillation pattern. On the contrast, neither Lac-ELPs nor Epidermal growth factor (EGF) was capable of evoking the same Ca2+ reaction in LGACs, which suggested Lac-ELPs and lacritin may trigger different signal transduction pathway other than utilizing second messenger Ca2+. It is possible that intracellular Ca2+ change was too low to be detected, on the basis that Lac-ELPs/lacritin caused lower β-hexosaminidase secretion in LGACs than carbachol (FIG. 11).

Example 14

Application of Lac-ELPs to Human Corneal Cells

Described herein is application of Lac-ELPs to corneal cells. SV40-immortalized HCE-T cells were grown to 80% confluent on glass bottom 35-mm dish in keratinocyte-SFM media (Life Technologies, Rockville, Md.) containing bovine pituitary extract (50 µg/ml), EGF (5 ng/ml) and penicillin/streptomycin. To optimize cell responsiveness to EGF and lacritin-ELPs, cells were starved with EGF and BPE free medium for 24 hours before experimentation.

The inventors observed the same Ca2+ wave pattern in HCE-T cells treated with Lac-ELPs and lacritin (FIGS. 15B3&B4). Interestingly, second messenger Ca2+ wrote a different code in HCE-T cells: instead of simultaneous twinkling scintillation, an obvious propagation wave of "brighten up" was observed across the cell sheet.

Compared to LGACs, elevation of intracellular Ca2+ concentration in HCE-T cells was sharper and decreased more smoothly, with a maximum 5 fold fluorescence increase in lacritin (10 µM) and Lac-S48I48 (40 µM) treating groups. Percentage of total responding cells was depending on lacritin/Lac-ELPs concentration (FIG. 15C). Moreover, HCE-T cells appeared to have "memory" for exogenous Lac/Lac-ELPs treatment, as treating the same group of cells for the second time with the same concentration of proteins, Ca2+ influx was higher (FIG. 15B4). The same Ca2+ wave pattern was observed in carbachol (FIG. 15A2) and EGF treatment groups (FIG. 15B2). While carbachol exhibited a concentration dependent effect; reaction of HCE-T cells to EGF was more biphasic, with maximum response recorded at 10 ng/ml (FIG. 15C). [Ca2+] elevation in HCE-T cells depended on extracellular-cytosol [Ca2+] gradient, as cells bathed in w/o Ca2+ solution did not respond to the same stimuli.

Example 15

Biostability of Lacritin

Lacritin crystals have been developed but are not yet suitable for X-ray diffraction. Without signal peptide, lacritin protein sequence itself has a calculated isoelectric point (pI) of 5.1715. Using ExPASy amino sequence composition analysis, composition of lacritin contains 10.9% Ser, 8.4% Thr, 9.2% Lys. With 10% Lys content, lacritin could easily be a serine protease target. At the same time, lacritin contains one His, thirteen Ser and three Asp, it may also exhibit autolysis property similar to trypsin. The described in vitro degradation results of purified lacritin show that half-life of lacritin is only 24 hours (FIG. 16A), which makes its purification a challenge.

As thermo-responsive biopolymer, ELPs show unique potential as a polypeptide "tag" for protein purification and as a carrier for therapeutic protein cargo. Compared with traditional His-tag and intein system, ELP system shows a more economic purification budget with satisfactory yield. In addition, scale-up of this purification method is easy because it is not limited by resin capacity. The method Inverse transition cycling (ITC) exploits the observation that proteins or peptides that are fused to a stimulus responsive ELP retain this behavior in the complex milieu of contaminating cellular components. In the described results, all control ELPs (V96, S96, I96, S48I48) show a yield of 50-100 mg/L (FIG. 5A). Due to fast degradation and pre-mature cleavage of ELP tag, a size-exclusion polishing step is required for lac-ELPs. But yield of the fusion protein is still over 30 mg/L. Removing ELP tag to release free lacritin is as simple as to trigger ELP phase transition and centrifuge it out of solution after thrombin cleavage (FIG. 5A). The inventors used thrombin kit from Sigma with thrombin attached to the agarose beads, thus during low speed centrifugation, thrombin was also removed from the supernatant, leaving only soluble lacritin.

Example 16

Signalling Pathways Involved in Prosecretory Activity

There are many therapeutics with great potential for ophthalmology but cannot be delivered in sufficiently high concentrations into the eye at the site of required action because of their improper size. The inventors have shown that fusion of lacritin with different ELPs, can improve in vitro pharmacokinetics and thus enhance therapeutic efficacy. Three types of ELP tags have been chosen to fulfill this aim: In the simplest form, S96 tag is fused to lacritin as a soluble macromolecular carrier. I96 and V96 as two hydrophobic tags with different Tt under 37° C. so that fusion protein forms a viscous coacervate, which may be used as insoluble drug depot when locally delivered at desired site. In a more sophisticated design, nanoscale self-assembly S48I48 block copolymer is chosen to assist Lac-ELP assemble into spherical micelles. Peroxidase secretion by rat lacrimal gland has been widely used for measuring protein secretion in vitro. However, it is not secreted by rabbit lacrimal gland, the most widely used animal model in vivo for evaluating secretion. β-hexosaminidase is present in both human and rabbit tear fluid and is secreted from rabbit lacrimal gland acinar cells in primary culture on stimulation with secretagogs. In this study, the inventors utilized this model to quantitatively evaluate prosecretory activity of Lac-ELPs and lacritin. Optimal rabbit LGACs response was observed after 1 hour Lac-ELP or lacritin treatment in a dose dependent manner, both showing 30-40% response compared to carbachol group.

To identify the impact of exogenous recombinant lac-ELP and lacritin on morphology change and mature secretion vesicle formation of LGACs, the inventors double transduced LGACs with adenovirus Ad-LifeAct-RFP (F-actin marker) and Ad-Syn-GFP (secretion protein marker) to observe cell response using confocal microscope. Ad-syncollin-GFP was generated and for amplification, QB1 cells, a derivative of HEK293 cells, were infected with Ad-syncollin-GFP and grown at 37° C. and 5% CO2 in DMEM (high glucose) containing 10% fetal bovine serum for 66 hours until completely detached from the flask surface. The Adeno-X™ virus purification kit was used for virus purification and the Adeno-X™ rapid titer kit for viral titration.

While carbachol triggered immediate intense F-actin remodeling beneath both apical and basal membrane of LGAC luminal region, Lac-ELPs and lacritin demonstrated a milder and more chronic effect, which suggests Lac-ELPs and lacritin signaling may involve other pathways other than activating muscarinic type 3 acetylcholine receptors (M3R). The inventors investigated signal transduction pathways triggered by Lac-ELP/lacritin stimuli by recording cytosolic Ca2+ wave change in LGACs and SV-40 transduced human corneal epithelial cells (HCE-Ts) stained with intracellular calcium indicator Fluo-4AM. While 10 μM carbachol treatment significantly elevated cytosolic Ca2+ level in LGACs, Ca2+ change in LGACs in regards to lacritin and Lac-ELPs treatments were hardly detected. Interestingly, Ca2+ wave propagation in HCE-T cells can be triggered by 10 μM lacritin/Lac-ELPs. Taken together, the prosecretory and elevating cytosolic [Ca2+] activities of Lac-ELPs supported our hypothesis that ELPs are promising as an ocular drug delivery carrier.

A better understanding of the complex spatiotemporal Ca2+ signal pattern in LGACs and HCE-T cells might therefore shed light on intracellular processes influencing lacritin and Lac-ELPs activity. The Ca2+ signaling results show that lacritin/Lac-ELPs did not exhibit the same Ca2+ oscillation pattern in LGACs as carbachol. Without being bound by any particular theory, this suggests a different downstream signaling pathway may be involved in its prosecretory activity. As a key regulator in maintaining corneal epithelial cell proliferation and migration, EGF was included in the Ca2+ signaling study, which acts in a paracrine fashion on epithelial cells proliferation via orchestrated calcium influx from intracellular calcium stores and extracellular space. EGF, carbachol and lacritin/Lac-ELPs exhibited similar Ca2+ wave pattern on HCE-T cells, which prompt us start wondering which cell receptors were involved in carbachol and EGF signaling. It is well known that carbachol stimulates tear fluid production through the activation of muscarinic receptors.

Compared to conventional synthetic low molecular weight drugs, proteins are more unstable during their storage and administration and susceptible to denaturation during the drug production process. Our degradation study of lacritin is an example of this concept.

Example 17

Discussion

To achieve minimal invasive means for the delivery of therapeutic proteins to treat dry eye disease is one of the challenges of ophthalmology. One obstacle of ocular drug delivery is the anatomical and physiological barriers in the eye and low bioavailability of present medications. Biodegradable polymer-based drug delivery systems show considerable promise for the treatment of ocular diseases by providing a sustained-release platform.

The results described herein demonstrate successful bioconstruction of lac-ELPs with versatile ELP tags and allowed us to potentially modulate in vitro and in vivo pharmacokinetic profile of native lacritin. β-hexosaminidase secretion results from our in vitro rabbit model also show promising therapeutic potential of lacritin-ELPs. Hydrophobicity of ELP tag did not show a significant impact on β-hexosaminidase secretion results. However, multivalent presentation of lacritin on the corona of ELP micelle decreased efficiency of lacritin proseretory activity. Lacritin-ELPs and lacritin induce chronic F-actin remodeling around acinar lumen and elevated mature secretion vesicle formation. Lac-ELPs and lacritin triggers transient Ca2+ waves in SV40-transduced Human Epithelial Cells (HCE-Ts).

The results herein described demonstrate construction of a lacritin-ELP fusion protein with biocompatible phase transition behavior without retardation of effective biological activity. The fusion protein imparts the thermo-responsive property of the ELP and prosecretory function of lacritin, which has great potential for controlling ocular bioavailability. This use of ELPs for constructing thermo-responsive ophthalmic drugs opens new possibilities for the treatment of dry eye disease.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods of preparing, isolating, or purifying fusion proteins containing bioresponse proteins polymers and/or therapeutic proteins, functional equivalents, and/or active fragments thereof, methods of treating various disease and/or conditions using fusion proteins, including types of diseases, conditions and/or target organ(s) that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. An isolated fusion protein comprising:
   a bioresponse protein polymer comprising an elastin-like polypeptide (ELP), and
   a therapeutic protein conjugated via a linker peptide to the bioresponse protein polymer, wherein the ELP comprises n number of amino acid motif SEQ ID NO: 19, where n comprises 10 to 300 units, and $X_{aa}$ of SEQ ID NO:19 is serine, valine, or isoleucine.

2. The isolated fusion protein of claim 1, wherein n is 96.

3. The isolated fusion protein of claim 1, wherein the therapeutic protein comprises lacritin or a functional equivalent.

4. The isolated fusion protein of claim 3, wherein the lacritin is human lacritin.

5. The isolated fusion protein of claim 3, wherein the lacritin or functional equivalent comprises amino acid sequence: SEQ ID NO: 3, SEQ ID NO: 4, SEQ ID NO: 5, SEQ ID NO: 6, SEQ ID NO: 7, or SEQ ID NO: 8.

6. The isolated fusion protein of claim 1, wherein the linker peptide comprises amino acid sequence: SEQ ID NO: 9.

7. The isolated fusion protein of claim 1, wherein the bioresponse protein polymer comprises an ELP, the therapeutic protein is lacritin, and the ELP is conjugated to the lacritin via a linker peptide.

8. An isolated polynucleotide encoding a fusion protein comprising:
   a bioresponse protein polymer comprising an elastin-like polypeptide (ELP), and
   a therapeutic protein conjugated to the bioresponse protein polymer via a linker peptide), wherein the ELP comprises n number of amino acid motif SEQ ID NO: 19, where n comprises 10 to 300 units and $X_{aa}$ of SEQ ID NO:19 is serine, valine, or isoleucine.

9. The isolated polynucleotide of claim 8, wherein n is 96 units.

10. A method of constructing the isolated polynucleotide of claim 8 using recursive directional ligation.

11. A method of enhancing ocular persistence of a therapeutic protein for treating a disease and/or condition in a human subject, comprising:
   providing a quantity of a composition, wherein the composition comprises the fusion protein of claim 1; and
   enhancing ocular persistence of the therapeutic protein for treating a human subject by administering a therapeutically effective dosage of the composition to the subject, wherein ocular persistence of the therapeutic protein conjugated to the bioresponse protein polymer is greater than ocular persistence of the therapeutic protein in the absence of conjugation to the bioresponse protein polymer.

12. The method of claim 11, wherein the human subject is in need of treatment for an eye disease and/or condition selected from the group consisting of: acanthamoeba keratitis, allergies, amblyopia, Bell's palsy, blepharitis, cataracts, chalazion, color blindness, corneal ulcer, detached retina, dry eye syndrome, keratoconjunctivitis sicca, eye occlusions, eye twitching, macular hole, nystagmus, ocular migraine, ocular rosacea, optic neuritis, optic neuropathy, photophobia, pinguecula, pterygium, ptosis, Sjogren's syndrome, strabismus, stye, subconjunctival hemorrhage, uveitis, CMV retinitis, conjunctivitis, diabetic retinopathy, eye herpes, glaucoma, karatoconus, macular degeneration, macular dystrophy, ocular hypertension, retinitis pigmentosa, and/or Stargardt's disease.

13. The method of claim 11, wherein the bioresponse protein polymer comprises an elastin-like polypeptide (ELP), the therapeutic protein comprises lacritin, and the ELP is conjugated to the lacritin via a linker peptide.

14. A pharmaceutical composition comprising:
   a bioresponse protein polymer comprising an elastin-like polypeptide (ELP), wherein the ELP comprises n number of amino acid motif SEQ ID NO: 19, where n comprises 10 to 300 units, and $X_{aa}$ of SEQ ID NO:19 is serine, valine, or isoleucine;
   a therapeutic protein conjugated to the bioresponse protein polymer via a linker peptide; and
   a pharmaceutically acceptable carrier.

15. The pharmaceutical composition of claim 14, wherein the therapeutic protein comprises lacritin.

* * * * *